US011285134B2

(12) United States Patent
Robinson et al.

(10) Patent No.: US 11,285,134 B2
(45) Date of Patent: *Mar. 29, 2022

(54) PRESBYOPIA TREATMENTS

(71) Applicant: Allergan, Inc., Irvine, CA (US)

(72) Inventors: Michael R. Robinson, Huntington Beach, CA (US); Mohammed Dibas, Corona, CA (US); Jaya Giyanani, Irvine, CA (US); Anuradha Gore, Aliso Viejo, CA (US); Sungwook Lee, Orange, CA (US); Haixia Liu, Irvine, CA (US); Aileen Morgan, Rancho Santa Margarita, CA (US); Jihao Zhou, Rancho Santa Margarita, CA (US)

(73) Assignee: ALLERGAN, INC., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/791,039

(22) Filed: Feb. 14, 2020

(65) Prior Publication Data

US 2021/0008034 A1 Jan. 14, 2021

Related U.S. Application Data

(63) Continuation of application No. 16/393,175, filed on Apr. 24, 2019, now Pat. No. 10,610,518.

(60) Provisional application No. 62/790,957, filed on Jan. 10, 2019, provisional application No. 62/780,117, filed on Dec. 14, 2018, provisional application No. 62/662,144, filed on Apr. 24, 2018.

(51) Int. Cl.
*A61K 31/4178* (2006.01)
*A61P 27/10* (2006.01)

(52) U.S. Cl.
CPC .......... *A61K 31/4178* (2013.01); *A61P 27/10* (2018.01)

(58) Field of Classification Search
CPC .......................... A61K 31/4178; A61P 27/10
See application file for complete search history.

(56) References Cited

U.S. PATENT DOCUMENTS

| 4,474,751 | A | 10/1984 | Haslam et al. |
|---|---|---|---|
| 4,851,521 | A | 7/1989 | della Valle et al. |
| 5,055,467 | A | 10/1991 | Albaugh |
| 5,122,522 | A | 6/1992 | Laties et al. |
| 5,422,116 | A | 6/1995 | Yen et al. |
| 5,459,133 | A | 10/1995 | Neufeld |
| 5,488,050 | A | 1/1996 | Neufeld |
| 5,574,518 | A | 11/1996 | Mercure |
| 5,612,361 | A | 3/1997 | Heyl et al. |
| 5,759,532 | A | 6/1998 | Galin et al. |
| 5,767,143 | A | 6/1998 | Lehmussaari et al. |
| 5,776,916 | A | 7/1998 | Gramer |
| 5,795,913 | A | 8/1998 | Lehmussaari et al. |
| 6,164,282 | A | 12/2000 | Gwon et al. |
| 6,218,428 | B1 | 4/2001 | Chynn |
| 6,273,092 | B1 | 8/2001 | Nolan |
| 6,291,466 | B1 | 9/2001 | Gwon et al. |
| 6,291,498 | B1 | 9/2001 | Horn |
| 6,410,544 | B1 * | 6/2002 | Gwon ............... A61K 31/00 514/256 |
| 6,420,407 | B1 | 7/2002 | Horn |
| 6,511,660 | B1 | 1/2003 | Lin et al. |
| 6,572,849 | B2 | 6/2003 | Shahinian, Jr. |
| 7,026,360 | B1 | 4/2006 | Festo |
| 7,666,894 | B2 | 2/2010 | Paborji |
| 7,678,821 | B2 | 3/2010 | Paborji |
| 7,767,429 | B2 | 8/2010 | Bookbinder et al. |
| 8,158,152 | B2 | 4/2012 | Palepu |
| 8,173,707 | B2 | 5/2012 | Demopulos et al. |
| 8,299,079 | B2 | 10/2012 | Kaufman |
| 8,455,494 | B2 | 6/2013 | Kaufman |
| 8,524,758 | B2 | 9/2013 | Benozzi |
| 8,829,037 | B2 | 9/2014 | Sharma |
| 8,859,623 | B1 | 10/2014 | Witham et al. |
| 9,089,560 | B2 | 7/2015 | Meyer |
| 9,089,562 | B2 | 7/2015 | Horn et al. |
| 9,301,933 | B2 | 4/2016 | Abad |
| 9,314,427 | B2 | 4/2016 | Horn et al. |
| 9,579,308 | B2 | 2/2017 | Abad |
| 9,579,385 | B2 | 2/2017 | Gore et al. |
| 9,623,007 | B2 | 4/2017 | Sharma |
| 9,682,147 | B2 | 6/2017 | Garrigue et al. |
| 9,867,810 | B1 | 1/2018 | Feinbaum et al. |
| 9,987,254 | B2 | 6/2018 | Hernandez et al. |
| 10,231,968 | B2 | 3/2019 | Hardten et al. |
| 2002/0035264 | A1 | 3/2002 | Kararli et al. |

(Continued)

FOREIGN PATENT DOCUMENTS

| AR | 081049 | 6/2012 |
|---|---|---|
| AU | 2015202175 | 5/2015 |

(Continued)

OTHER PUBLICATIONS

Kambhampati, Center for Drug Evaluation and Research, NDSA-200-890, Chemistry Review, 2010. (Year: 2010).*
Abelson, M.B., et al., Demystifying Dumulcents: A look at the varities of this common agent and how they can help soothe patients' eyes, Rev. Ophthal., 2006, pp. 1-5.
Akers, M.J., Antioxidants In Pharmaceutical Products, Journal of Parenteral Science and Technology, vol. 36 No. 5, 1982, pp. 222-228.
Allingham, et al., Cholingeric Agents, Shield's Textbook of Glaucoma, 2005, 501-506, Chap. 33, Lippincott Williams & Wilkins, Philadelphia.
Ambramson, D.H., et al., Pilocarpine-Induced Lens Changes: An Ultrasonic Biometric Evaluation of Dose Response, Arch. Ophthalmology, 1974, 464-469, 92.
Ambramson, D.H., et al., Pilocarpine: Effect on the Anterior Chamber and Lens Thickness, Arch. Ophthalmology, 1972, 615-620, 87.
Beasley, H., et al., Retinal Detachments and Topical Ocular Miotics, Symposium on Drugs, 1979, 95-98, 86.

(Continued)

*Primary Examiner* — Jean P Cornet
(74) *Attorney, Agent, or Firm* — Lorenz Siddiqi

(57) ABSTRACT

Described herein are methods and compositions for the treatment of ocular conditions and for the improvement of vision parameters using pharmaceutically acceptable ophthalmic pilocarpine formulations. A nonlimiting example of an ocular condition that may be treated with the methods and compositions disclosed herein is presbyopia.

36 Claims, 13 Drawing Sheets

(56) References Cited

U.S. PATENT DOCUMENTS

| | | |
|---|---|---|
| 2003/0139737 A1 | 7/2003 | Lin |
| 2004/0078009 A1 | 4/2004 | Lin |
| 2004/0106644 A1 | 6/2004 | Randazzo |
| 2004/0137068 A1 | 7/2004 | Bhushan |
| 2005/0205101 A1 | 9/2005 | Lin |
| 2005/0261641 A1 | 11/2005 | Warchol et al. |
| 2005/0279369 A1 | 12/2005 | Lin |
| 2006/0177430 A1 | 8/2006 | Bhushan et al. |
| 2006/0184243 A1 | 8/2006 | Yilmaz |
| 2007/0053964 A1 | 3/2007 | Isowaki et al. |
| 2007/0211212 A1 | 9/2007 | Bennwik |
| 2008/0076828 A1 | 3/2008 | Dalton et al. |
| 2009/0156606 A1 | 6/2009 | Sharma |
| 2012/0028910 A1 | 2/2012 | Combal et al. |
| 2014/0024642 A1 | 1/2014 | Vejarano Restrepo |
| 2015/0010634 A1 | 1/2015 | Knappe et al. |
| 2015/0174105 A1 | 6/2015 | Hernandez et al. |
| 2015/0196541 A1 | 7/2015 | Shams et al. |
| 2016/0008337 A1 | 1/2016 | Horn et al. |
| 2017/0007637 A1 | 1/2017 | Feinbaum et al. |
| 2017/0112939 A1 | 4/2017 | Knappe et al. |
| 2018/0098937 A1 | 4/2018 | Horn |
| 2018/0147214 A1 | 5/2018 | Ostrow et al. |
| 2018/0221274 A1 | 8/2018 | Meyer |
| 2018/0318264 A1 | 11/2018 | Feinbaum et al. |

FOREIGN PATENT DOCUMENTS

| | | |
|---|---|---|
| CN | 1311670 A | 9/2001 |
| CN | 107847432 | 3/2018 |
| EP | 0507224 | 10/1996 |
| EP | 1173207 | 1/2002 |
| EP | 11004801 | 9/2003 |
| EP | 1938839 | 8/2009 |
| EP | 2630952 | 8/2013 |
| EP | 28886113 | 6/2015 |
| WO | 9325199 | 12/1993 |
| WO | 9410976 | 5/1994 |
| WO | 0044379 | 8/2000 |
| WO | 0064425 A2 | 11/2000 |
| WO | 2005021004 | 3/2005 |
| WO | 2008075149 | 6/2008 |
| WO | 2009077736 | 6/2009 |
| WO | 2009077736 A3 | 6/2009 |
| WO | 2009077736 A4 | 6/2009 |
| WO | 2010125416 | 11/2010 |
| WO | 2010135731 | 11/2010 |
| WO | 2011013794 | 2/2011 |
| WO | 2014015183 | 1/2014 |
| WO | 2017011271 | 1/2017 |
| WO | 2017115238 | 7/2017 |

OTHER PUBLICATIONS

Benedict, W.L., et al., Impending Macular Hole Associated with Topical Pilocarpine, Am. J. Ophthalmology, 1992, 765-766, 114(6).

Boger, W. et al., Clinical Trial Comparing Timolol Ophthalmic Solution to Pilocarpine In Open-Angle Glaucoma, Am. J. Opthalmol., 1978, 8-18, 86.

Brown, H.S., et al., Visual Effects of Pilocarpine in Glaucoma, Arch. Ophthalmol., 1976, 1716-1719, 94.

Diestelhorst,M., The additive intraocular pressure-lowering effect oof latanoprost 0.005% daily once and pilocarpine 2% t.i.d. in pateinst with open-angle glaucoma or ocular hypertension: A 6-month, randomized, mulitcenter study, Graefe's Arch Clin Exp Ophthalmol, 2000, 433-439, 238.

Edelhauser, H.F., et al., Corneal Edema and the Intraocular Use of Epinephrine, Am. J. Ophthalmology, 1982, 327-333, 93.

Evans et al., Agonist-specific coupling of G-protein-coupled receptors to second-messenger systems, Progress in Brain Research, vol. 106, 1995, pp. 259-268.

Food & Drug Admin., Challenge and Opportunity on the Critical Path to New Medical Technologies, Mar. 2004, 24, US Dept. of Health & Human Services, Washington, D.C.

Food & Drug Administration, Isopto Carpine Prescribing Information, FDA Access Data, 2006, 5 pages.

Francois, J., et al., Ultrasonographic Study of the Effect of Different Miotics on the Eye Components, Ophthalmologica (Basel), 1977, 328-338, 175.

Fuder, Hermann, Functional Consequences of Prejunctional Receptor Activation or Blockade in the Iris, Journal of Ocular Pharmacology, vol. 10, No. 1, pp. 109-123.

Garcia-Lozara, S., et al., Visual function through 4 contact lens-based pinhole systems for presbyopia, J. Cataract Refract. Surg., 2012, 858-865, 38 (5).

Gibbs, I.S., et al., Formulation of a Stable Pilocarpine Hydrochloride Solution, J. Pharma. Sci., 1974, 276-279, 63 (2).

Gilmartin et al., Reversal of tropicamide mydriasis with single Instillations of pilocarpine can induce sustantial pseudo-myopia in young adults, Ophthalmic and Physiological Optics, vol. 15, No. 5, pp. 475-479.

Glasser, A., Accommodation and Presbyopia, In: Adler's Physiology of the Eye, 2003, University of Houston, Houston, TX.

Hall, J.Q., et al., Visual Effect and Residence Time of Artificial Tears in Dry Eye Subjects, Optom. Vis. Sci, 2011, 872-880, 88.

Harbin, T., et al., Comparative Intraocular Pressure Effects of Adsorbocarpine and Isoptocarpine, Annals of Ophthalmology, 1978, 59-61, 10.

Harris, L., et al., Effect of Ocular Pigmentation on Hypotensive Response to Pilocarpine, American Journal of Ophthalmology, 1971, 923-928, 5.

Hickenbotham et al., Comparison of spherical aberration and small-pupil profiles in improving depth of focus for presbyopic corrections, J. Cataract Refract. Surg., vol. 38, No. 12, Dec. 2012, pp. 2071-2079.

Holden, B.A, et al., Global vision impairment due to uncorrected presbyopia, Arch. Ophthalmology, 2008, 1731-1739, 126.

International Search Report and Written Opinion issued for PCT/IB12/02335 filed Sep. 19, 2012 in the name of Allergan, Inc.

Johnson, L., et al., Multifocal spectacles increase variability in toe clearance and risk of tripping in the elderly, IVOS, 2007, 1466-1471, 48.

Järvinen, K., et al., The effect of a modified β-cyclodextrin, SBE4-β-CD, on the aqueous stability and ocular absorption of pilocarpine, Curr. Eye Res., 1994, 897-905, 13.

Kenakin, Terry, Agonist-receptor efficacy II: agonist trafficking of receptor signals, Trends in Pharmacological Sciences, vol. 16, 1995 pp. 232-238.

Kini, M., et al., Echothiophate, Pilocarpine, and Open-Angle Glaucoma, Arch. Ophthalmol., 1973, 190-192, 89.

Lachman, Leon, Antioxidants and Chelating Agents as Stabilizers in Liquid Dosage Forms—Part 1, Drug and Cosmetic Industry, vol. 102, 1968, pp. 36-38, 40 and 146-148.

Levin, et al., Adler's Physiology of the Eye, 2011, 44-57, 289-291, & 509-510, 11, Saunders Elsevier, Edinburgh.

Lord, S.R., et al., Multifocal glasses impair edge-contrast sensitivity and depth perception and increase the risk of falls in older people, J. Am. Geriatric Society, 2002, 1760-1766, 50.

Miller, R., et al., How Modeling and Simulation have Enhanced Decision Making in New Drug Development, Journal of Pharmacokinetics and Pharmacodynamics, 2005, 185-197, 32 (2).

Moishirfar, M., et al., Comparison of FDA safety and efficacy data for KAMRA and Raindrop corneal Inlays, Int. J. Ophthalmol., 2017, 1446-1451, 10 (9).

Morrison, H.W., Stability of Aqueous Solutions Commonly Employed in the Treatment of Primary Glaucoma, Aqueous Solutions for Glaucoma, 1954, 744-758.

Norvatis Pharmaceuticals Canada Inc., Isopto Carpine, Prescribing Information & Consumer Information, 2016, pp. 1-12.

Novitskaya et al., Effect of some ophthalmic medications on pupil size: a literature review, Can. J. Ophthalmol., vol. 44, No. 2, 2009, pp. 193-197.

Ostrin et al., Accommodation measurements in a prepresbyopic and presbyopic population, J. Cataract Refract. Surg., vol. 30, 2004, pp. 1435-1444.

(56) References Cited

OTHER PUBLICATIONS

Pape, L.G., et al., Retinal Detachment and Miotic Therapy, Am. J. Ophthalmology, 1978, 558-566, 85.

Phillips, C.I., Conservative Management of the Glaucomas, Trans Ophthalmol. Soc. U.K., 1966, 233-245, 89.

Puustjarvi, T., Retinal Detachment during Glaucoma Therapy; Review. A Case report of an Occurrence of Retinal Detachment after Using Membranous Pilocarpine Delivery System [Pilokarpin Lameller (Ocusert®) 11 mgl, Ophthalmologica (Basel), 1985, 40-44, 190.

Quigley, H., et al., Intraocular Pressure Control with Twice-daily Pilocarpine in Two Vehicle Solutions, Annals of Ophthalmology, 1977, 427-430, 9.

Randazzo, A., et al., Pharmacological management of night vision disturbances after refractive surgery : Results of a randomized clinical trial, J. Cataract Refract. Surg., 2005, 1764-7772, 31.

Reddy, I., et al., Topical Ophthalmic Formulations: Basic Considerations, Ocular Therapeutics & Drug Delivery: A Multidisciplinary Approach, 1996, Chap. 13: 387-389, Technomic Publishing Co., Inc., Lancaster.

Ritch, R., et al., Ocular Cholingeric Agents, The Glaucomas, 1989, Chap. 24: 515-521, The C.V. Mosby Co., St. Louis.

Romano, J.H., Double-blind cross-over comparison of aceclidine and pilocarpine in open-angle glaucoma, Brit. j. Ophthal., 1970, 510-520, 54.

Ruiz, L.A., et al., Intrastromal correction of presbyopia using femtosecond laser system, J. Refract. Surg., 2009, 847-854, 25 (10).

Shell, John, Ophthalmic Drug Delivery Systems, Survey Ophthalmol., 1984, 117, 29.

Tomita, M., Advances in Implantation Over the Years, Cataract Refract. Surg. Today, 2015, 67-68, retrieved from https://crstoday.com/articles/2015-jun/advances-in-implanation-over-the-years on Mar. 5, 2019.

Tsai, J.C., et al., Medical Management of Glaucoma, 2009, 109, 159, 191, & 225, 3rd Ed., Professional Communications, Inc., West Islip, New York.

Tucker, J. et al., The depth-of-focus of the human eye for Snellen letters, Am. J. Optom. Physiol. Opt., 1975, 3-21, 52 (1).

Walker, J.D., et al., Vitreofoveal traction associated with the use of pilocarpine to reverse mydriasis, Eye, 2007, 1430-1431, 21.

Wang et al., Review of Excipients and pHs for Parenteral Products Used in the United States, Journal of the Parenteral Drug Association vol. 34, No. 6, 1980, pp. 452-462.

Wang et al., Supplement 1988, Parenteral Formulations of Proteins and Peptides: Stability and Stabilizers, J. Parent. Sci. and Tech., 42:S4-S26.

Akron Pharmaceuticals, Pilocarpine Hydrochloride Ophthalmic Solution, USP 1%, 2% and 4%, 2017, pp. 2.

Aldrich et al. Stimuli to the revision process, vol. 39(5) Sep.-Oct. 2013.

Chambers, W., Summary Review of NDA 200-890, US Food & Drug Admin., 2010, 1-7.

Nakada, Y., Analysis of Development History of Medical Glaucoma Eye Drops, Pharmaceutics, 2015, 65-71, 75 (1).

Tan, A., et al., The fixed dilated pupil after cataract surgery—is it related to intraocular use of hypromellose?, British J. Ophthalmol., 1993, 639-641, 77.

Unknown, Drug Interview Form for Sanpilo, Japan Hospital Association, 2017, 31 pages, partial English translation.

Alcon Laboratories, Inc., Isopto Carpine label, revised 2010, pp. 1-5.

Green, K., et al., Ocular Penetration of Pilocarpine in Rabbits, Arch. Opthalmol., 1975, 1165-1168, 93.

Scholz, M., et al., Pilocarpine Permeability across Ocular Tissues & Cell Cultures: Influence of Formulation Parameters, J. Ocular Pharmacol. Thera., 2002, 455-470, 18 (5), \* cited by examiner

PRESBYOPIA TREATMENTS

PRIORITY

This application is a continuation of U.S. patent application Ser. No. 16/393,175, filed Apr. 24, 2019, which claims the benefit of priority from U.S. Provisional Patent Application Ser. No. 62/662,144, filed Apr. 24, 2018, U.S. Provisional Patent Application Ser. No. 62/780,117, filed Dec. 14, 2018, and U.S. Provisional Patent Application Ser. No. 62/790,957, filed Jan. 10, 2019, the disclosures of which are hereby incorporated in their entireties herein by reference.

BACKGROUND

Presbyopia and other visual disorders have long been treated primarily with optical lenses and other such mechanical devices. As discussed in further detail herein, it would be advantageous to provide an alternative treatment that would avoid the use of such devices and the various disadvantages that these entail.

Cholinergic agonists, such as pilocarpine, have been used to lower intraocular pressure ("IOP") so as to treat primary open angle glaucoma. Such cholinergic agonists were a mainstay for treatments that sought to lower IOP until the introduction of timolol in 1978. In the subsequent decades, and with the introduction of topical carbonic anhydrase inhibitors, alpha agonists, and prostaglandin agonists, pilocarpine became prescribed less often since the newer drugs had a much lower incidence of side effects such as reduced visual acuity and ocular discomfort (Allingham et al., Shields' Textbook of Glaucoma, 5$^{th}$ edition, Lippincott Williams & Wilkins (Philadelphia), 2005, pp. 501-503).

BRIEF SUMMARY

Described herein are compositions and methods for improving vision using pilocarpine.

In some embodiments, there is provided a method of treating an ocular condition in a patient comprising administering to the patient an ophthalmic composition comprising pilocarpine hydrochloride.

In one preferred embodiment, there is provided a method of treating an ocular condition in a patient in need thereof, comprising administering to the patient a pharmaceutically acceptable ophthalmic composition comprising pilocarpine hydrochloride at a concentration from 1.0 to 1.5% w/v, wherein the formulation is administered topically to at least one eye of the patient, and wherein the ocular condition is selected from the group consisting of presbyopia, hyperopia, mydriasis, anisocoria, accommodative esotropia, myopia, and astigmatism.

In another preferred embodiment, there is provided a method of improving at least one vision parameter in a patient in need thereof, comprising administering to the patient a pharmaceutically acceptable ophthalmic composition comprising pilocarpine hydrochloride at a concentration from 1.0 to 1.5% w/v, wherein the formulation is administered topically to at least one eye of the patient, and wherein the at least one vision parameter is selected from the group consisting of near vision acuity, intermediate vision acuity, distance vision acuity, night vision, day vision, glare, and light scattering.

In a further preferred embodiment, there is provided a method for improvement of near vision in a patient with presbyopia in need thereof, comprising administering to an eye of the patient a pharmaceutically acceptable ophthalmic composition comprising pilocarpine hydrochloride at a concentration from 1.0 to 1.5% w/v.

In some embodiments, the ocular condition is presbyopia. In some embodiments, the ocular condition is hyperopia. In some embodiments, the ocular condition is mydriasis. In some embodiments, the vision parameter is near vision acuity. In some embodiments, the vision parameter is intermediate vision acuity. In some embodiments, the vision parameter is distance vision acuity. In some embodiments, the vision parameter is night vision. Additional embodiments provide for the method resulting in an at least 3-line improvement from baseline under the condition of mesopic, high contrast UNVA. In some embodiments, the method results in an at least 2-line improvement from baseline under the condition of mesopic, high contrast UNVA. In some embodiments, the method results in an increase in the average letter change from baseline under the condition of mesopic, high contrast UNVA. In some embodiments, the method results in an at least 2-line improvement from baseline under the condition of photopic, high contrast UNVA. In some embodiments, the method results in an at least 2-line improvement from baseline under the condition of photopic, high contrast UDVA. In some embodiments, the method results in an at least 3-line improvement from baseline under the condition of mesopic, high contrast DCNVA. The method may result in an at least 3-line improvement from baseline under the condition of photopic, high contrast DCNVA. In some embodiments, the method results in an at least 3-line improvement from baseline under the condition of mesopic, high contrast DCIVA. The method may result in an at least 3-line improvement from baseline under the condition of photopic, high contrast DCIVA. In some embodiments, the method results in an improvement of at least one line in at least one selected from the group consisting of UNVA, UDVA, DCNVA, and DCIVA.

Further embodiments provide for the pharmaceutically acceptable ophthalmic composition to comprise pilocarpine hydrochloride at a concentration that is greater than or equal to 1% and less than 1.5% w/v. The pharmaceutically acceptable ophthalmic composition may comprise pilocarpine hydrochloride at a concentration of 1.25% w/v. Some embodiments provide for pilocarpine hydrochloride being the sole active ingredient in the pharmaceutically acceptable ophthalmic composition. In some embodiments, the pharmaceutically acceptable ophthalmic composition does not comprise a polymer. Administration of the pharmaceutically acceptable ophthalmic composition may in some embodiments result in a lower incidence of at least one of ocular blurring, ocular discomfort, eye pain, brow ache, blurry vision, light sensitivity, stinging, and itching, compared to administration of a second ophthalmic composition comprising pilocarpine and a polymer. In some embodiments, the pharmaceutically acceptable ophthalmic composition further comprises boric acid, sodium citrate dihydrate, sodium chloride, hydrochloric acid and/or sodium hydroxide, and water. The pharmaceutically acceptable ophthalmic composition may be administered once daily. The pharmaceutically acceptable ophthalmic composition may be administered twice daily. The pharmaceutically acceptable ophthalmic composition may be administered to both eyes of the patient. The pharmaceutically acceptable ophthalmic composition may be administered to one eye of the patient. The pharmaceutically acceptable ophthalmic composition may be administered to the nondominant eye of the patient. The pharmaceutically acceptable ophthalmic composition may be administered to the dominant eye of the patient.

An additional preferred embodiment provides for a composition for the treatment of an ocular condition, wherein the composition is pharmaceutically acceptable and comprises pilocarpine hydrochloride at a concentration from 1.0 to 1.5% w/v, and wherein the ocular condition is selected from the group consisting of presbyopia, hyperopia, mydriasis, anisocoria, accommodative esotropia, myopia, and astigmatism.

In some embodiments, the composition comprises 1.25% w/v pilocarpine hydrochloride, and the ocular condition is presbyopia. In some embodiments, the composition comprises 1.25% w/v pilocarpine hydrochloride, boric acid, sodium citrate dihydrate, sodium chloride, hydrochloric acid and/or sodium hydroxide, and water. In further embodiments, the composition is applied once daily. The composition may be applied twice daily. The composition may be administered to both eyes of a patient. The composition may be administered to a nondominant eye of a patient. The composition may be administered to a dominant eye of a patient. In some embodiments, pilocarpine hydrochloride is the sole active ingredient. Some embodiments, may further comprise a preservative. The preservative may be benzalkonium chloride. In certain embodiments, the composition comprises about 1.25% w/v pilocarpine hydrochloride, about 1.0% w/v boric acid, about 0.015% w/v sodium citrate dihydrate, about 0.08% w/v sodium chloride, and about 0.0075% w/v benzalkonium chloride. The composition may consist essentially of 1.25% w/v pilocarpine hydrochloride, 1.0% w/v boric acid, 0.015% w/v sodium citrate dihydrate, 0.08% w/v sodium chloride, and 0.0075% w/v benzalkonium chloride, with a pH of 5.0. The composition in some embodiments reduces the incidence of at least one adverse event selected from the group consisting of ocular blurring, ocular discomfort, eye pain, brow ache, blurry vision, light sensitivity, ocular stinging, and ocular itching, compared to administration of a second ophthalmic composition comprising pilocarpine and a polymer. The second composition may comprise 1% w/v pilocarpine and the polymer may be hydroxy propyl methyl cellulose.

In yet another preferred embodiment, there is provided a composition for improving at least one vision parameter, wherein the composition is pharmaceutically acceptable and comprises pilocarpine hydrochloride at a concentration from 1.0 to 1.5% w/v, and wherein the at least one vision parameter is selected from the group consisting of near vision acuity, distance vision acuity, night vision, day vision, glare, and light scattering.

In some embodiments, the composition comprises 1.25% w/v pilocarpine hydrochloride, and the vision parameter is near vision acuity. The composition may comprise 1.25% w/v pilocarpine hydrochloride, and the vision parameter may be distance vision acuity. The composition may comprise 1.25% w/v pilocarpine hydrochloride, boric acid, sodium citrate dihydrate, sodium chloride, hydrochloric acid and/or sodium hydroxide, and water. The composition may be applied once daily. The composition may be applied twice daily. In some embodiments, the composition is administered to both eyes of a patient. The composition may be administered to a nondominant eye of a patient. In some embodiments, the composition may be administered to a dominant eye of a patient. In some embodiments, pilocarpine hydrochloride is the sole active ingredient. The composition may further comprise a preservative. The preservative may be benzalkonium chloride. In some embodiments, the composition comprises about 1.25% w/v pilocarpine hydrochloride, about 1.0% w/v boric acid, about 0.015% w/v sodium citrate dihydrate, about 0.08% w/v sodium chloride, and about 0.0075% w/v benzalkonium chloride. In some embodiments, the composition consists essentially of 1.25% w/v pilocarpine hydrochloride, 1.0% w/v boric acid, 0.015% w/v sodium citrate dihydrate, 0.08% w/v sodium chloride, and 0.0075% w/v benzalkonium chloride, with a pH of 5.0.

In another preferred embodiment, there is provided a composition for the improvement of near vision in a patient with presbyopia, wherein the composition is pharmaceutically acceptable and comprises pilocarpine hydrochloride at a concentration from 1.0 to 1.5% w/v.

In some embodiments, the composition comprises 1.25% w/v pilocarpine hydrochloride, and the ocular condition is presbyopia. In some embodiments, the composition comprises 1.25% w/v pilocarpine hydrochloride, boric acid, sodium citrate dihydrate, sodium chloride, hydrochloric acid and/or sodium hydroxide, and water. The composition may be administered once daily. In some embodiments, pilocarpine hydrochloride is the sole active ingredient. The composition may further comprise a preservative. The preservative may be benzalkonium chloride. In another embodiment, the composition comprises about 1.25% w/v pilocarpine hydrochloride, about 1.0% w/v boric acid, about 0.015% w/v sodium citrate dihydrate, about 0.08% w/v sodium chloride, and about 0.0075% w/v benzalkonium chloride. In yet another embodiment, the composition consists essentially of 1.25% w/v pilocarpine hydrochloride, 1.0% w/v boric acid, 0.015% w/v sodium citrate dihydrate, 0.08% w/v sodium chloride, and 0.0075% w/v benzalkonium chloride, with a pH of 5.0.

In a preferred embodiment, there is provided a composition for the improvement of near vision in a patient with presbyopia, the composition comprising 1.25% w/v pilocarpine hydrochloride, 1.0% w/v boric acid, 0.015% w/v sodium citrate dihydrate, 0.08% w/v sodium chloride, 0.0075% w/v benzalkonium chloride, and water, with a pH of 3.0-5.5.

In some embodiments, the composition consists of 1.25% w/v pilocarpine hydrochloride, 1.0% w/v boric acid, 0.015% w/v sodium citrate dihydrate, 0.08% w/v sodium chloride, 0.0075% w/v benzalkonium chloride, and water, with a pH of 5.0. In some embodiments, the composition is topically administered to the patient once daily.

In yet another preferred embodiment, a method for the improvement of near vision in a patient with presbyopia comprises administering to at least one eye of the patient a pharmaceutically acceptable ophthalmic composition comprising pilocarpine as the sole active ingredient, wherein said composition does not contain any viscosity-enhancing polymers.

In some embodiments, the composition comprises pilocarpine hydrochloride. The composition may comprise 1.25% w/v pilocarpine hydrochloride. In some embodiments, the composition comprises pilocarpine nitrate. In further embodiments, the composition comprises 1.25% w/v pilocarpine hydrochloride or a molar equivalent pilocarpine salt. The composition may be administered once daily. The composition may be administered twice daily. In some embodiments, the composition is administered to a nondominant eye of the patient. In some embodiments, the composition is administered to a dominant eye of the patient. The composition may also be administered to both eyes of the patient. In some embodiments, the composition does not contain hydroxy propyl methyl cellulose. In further embodiments, administration of the pharmaceutically acceptable composition reduces the incidence of one or more adverse events compared to the administration of a pilocarpine composition comprising one or more viscosity-enhancing polymers. The one or more adverse events may be selected from the group consisting of ocular blurring, ocular discomfort, eye pain, brow ache, blurry vision, light sensitivity, ocular stinging, and ocular itching.

In a further preferred embodiment, there is provided a method comprising administering to at least one eye of a patient with presbyopia a pharmaceutically acceptable ophthalmic composition comprising a first amount of pilocarpine hydrochloride as the sole active ingredient, wherein such administration is made without previously administering a second amount of pilocarpine hydrochloride and/or subsequently administering a third amount of pilocarpine hydrochloride; wherein the second amount is lower than the first amount, and wherein the third amount is higher than the first amount.

In some embodiments, the first amount of pilocarpine hydrochloride is 1.25% w/v. The pharmaceutically acceptable ophthalmic composition may be administered to both eyes of the patient. The pharmaceutically acceptable ophthalmic composition may be administered once daily, or twice daily.

DETAILED DESCRIPTION

Definitions

Figure 1:
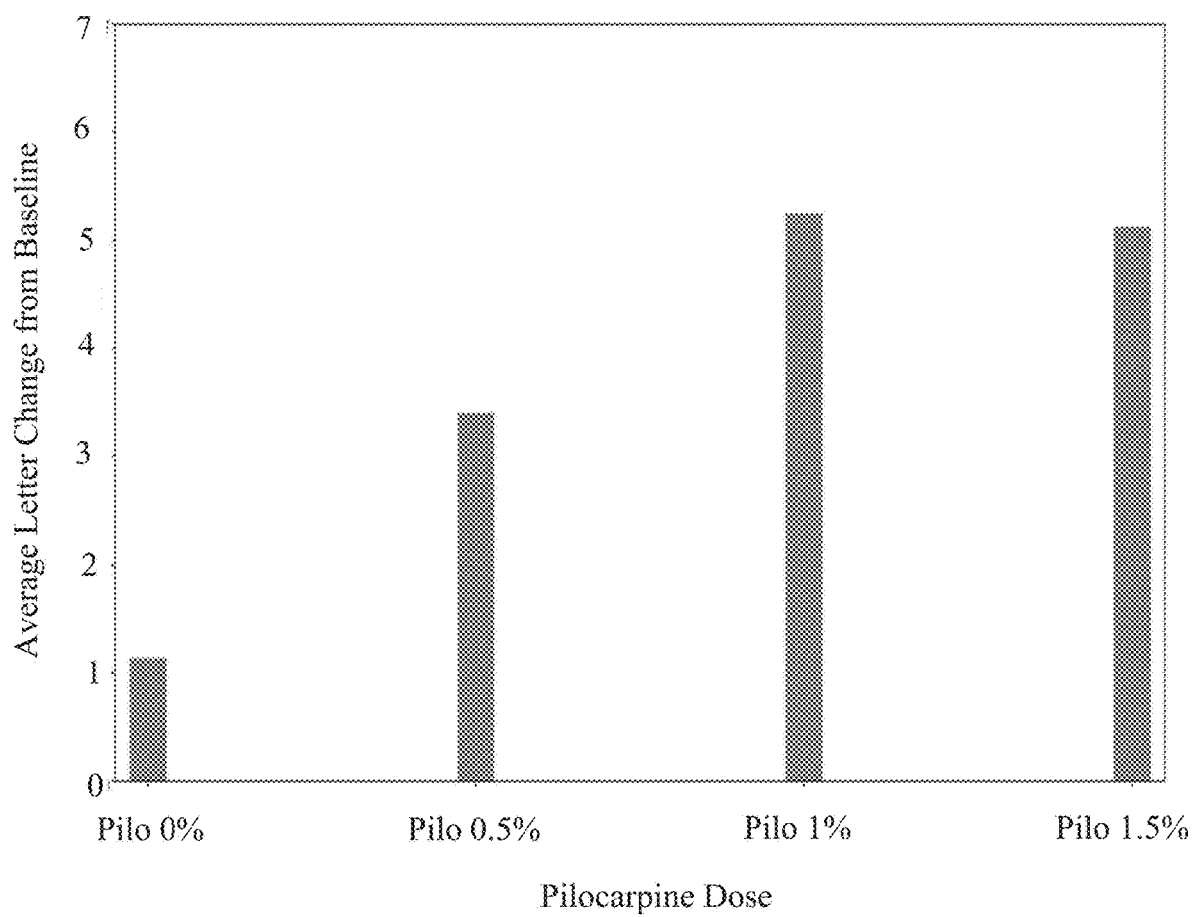
FIG. 1 shows the average change from baseline of number of letters in mesopic UNVA (mITT, non-dominant eye, Clinical Study B using ANCOVA).

Unless defined otherwise, all technical and scientific terms used herein have the same meaning as commonly understood by one of ordinary skill in the art to which the subject matter pertains.

In describing and claiming the present subject matter, the following terminology will be used in accordance with the definitions set out below.

As used in this specification and the appended claims, the singular forms "a," "an" and "the" include plural referents unless the context clearly dictates otherwise.

The term "therapeutically effective amount" refers to an amount that is effective, when administered to an individual to treat one or more ocular conditions and/or improve at least one vision parameter. The extent of the vision improvement and/or success in the treatment of the ocular condition when a therapeutically effective amount of a compound and/or composition is administered to an individual would be readily identifiable to a skilled person as is described herein.

The term "uncorrected near visual acuity" ("UNVA") refers to a person's ability, without any vision aid (such as eyeglasses or contact lenses), to see the details of objects within arm's distance from the body (e.g., at 33-41 cm away from the eye). Similarly, the term "distance corrected near visual acuity" ("DCNVA") may be used to refer to a person's ability to see the details of objects within arm's distance from the body (e.g., at 33-41 cm away from the eye), with the use of vision aids such as eyeglasses or contact lenses that correct for distance vision issues. The terms "near visual acuity", "near vision acuity", and "near vision" may be used interchangeably.

The term "uncorrected distance visual acuity" ("UDVA") refers to a person's ability, without any vision aid (such as eyeglasses or contact lenses), to see the details of objects beyond arm's distance from the body (e.g., greater than 4 meters away from the eye The terms "distance visual acuity", "distance vision acuity", and "distance vision" may be used interchangeably.

The terms "intermediate vision", "intermediate vision acuity", and "intermediate visual acuity" may be used to refer to a person's ability to see the details of objects at distances between the near and far visual ranges. In other words, such a distance range would be between a distance approximately farther than arm's distance (about 33-41 cm away from the eye) and less than approximately 4 meters from the eye. In some embodiments, for example, this may refer to the distance from a person's eye to an object near a person's feet. The term distance-corrected intermediate visual acuity ("DCIVA") may be used to refer to a person's ability to see the details of objects at intermediate distances with the use of vision aids such as eyeglasses or contact lenses that correct for distance vision issues.

The term "2-line improvement from baseline" or "3-line improvement from baseline" or similar improvement from baseline refers to a person's ability to read 2 or 3 more lines of letters on a standard chart (e.g., Snellen, ETDRS, Logarithmic Visual Acuity Chart, etc.) after treatment with pilocarpine when comparing to the number of lines readable before treatment.

The term "the number of letters correctly read" refers to the number of letters on a standard chart (e.g., Snellen, ETDRS, Logarithmic Visual Acuity Chart, etc.) that can be correctly read by a person. The term "increase from baseline in the number of letters correctly" refers to the increase from pre-treatment in the number of letters correctly read at certain post treatment time point.

The term "mITT" refers to the modified intent-to-treat population, which is defined as all randomized patients with a baseline and at least 1 post baseline assessment of mesopic, high contrast, UNVA, and with a baseline UNVA of no greater than 3 lines across the 5 dosing periods.

The term "vision parameter" may refer to any characteristic in a patient's vision that may be measured and is susceptible to being improved by the compositions and methods described herein. Vision parameters that may be improved in the various embodiments described herein include but are not limited to near vision acuity, intermediate visual acuity, distance visual acuity, night vision, day vision, optical aberrations (e.g., glare, light scattering), and uncorrected refractive errors. Additional examples of vision parameters that may be improved in the various embodiments described herein also include without limitation night time glare, post-LASIK "star burst" glare, visual "halos" seen around light sources, and accommodative insufficiency.

Vision or visual improvement, including but not limited to near, intermediate, and/or distance visual acuity, may for example be reflected in the increase of number of letters correctly read at any time point post dosing, the increase in the average letter change, or 2-line or 3-line improvement, all from baseline (i.e., from pre-treatment). Night vision improvement may be reflected in visual improvement for patients in dim or dark lighting (e.g., under mesopic or scotopic conditions). Day vision improvement may be reflected in visual improvement for patients in bright lighting as found during daylight hours or in sunshine (e.g., under photopic conditions). Vision improvement using the embodiments described herein may also be achieved in combination with or when using other visual aids and devices (especially those used for treating presbyopia), including but not limited to reading glasses, lens modifying medications, and surgical presbyopic options including intraocular lenses (IOLs).

The term "ocular condition" may refer to any condition, disease, or impairment which affects or involves the eye or one of the parts or regions of the eye, and includes optical issues causing refractive errors in the eye. Ocular conditions include, but are not limited to presbyopia, hyperopia, mydriasis, anisocoria, and accommodative esotropia, myopia, astigmatism, Adie's tonic pupil, or other causes of parasympathetic denervation, accommodative insufficiency, and complications arising after refractive surgery, such as decentered ablations following LASIK or PRK, corneal scars, hazing, refractive errors, and so forth.

Pilocarpine is a cholinergic muscarinic agonist represented by the following chemical structure:

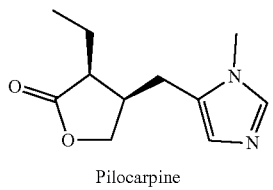

Pilocarpine

Pilocarpine may present in different salt forms, but is typically used with its hydrochloride salt. Other possible salts include, but are not limited to, nitrate, hydrate, and free acids. Unless specified otherwise, references to "pilocarpine" herein will mean "pilocarpine hydrochloride".

Additionally, references herein to compositions with pilocarpine, unless otherwise specified, should be interpreted as such an amount of a composition with pilocarpine hydrochloride in units of weight per volume. For example, 1.25% pilocarpine would mean a composition of 1.25% w/v pilocarpine hydrochloride.

In the embodiments described herein, pilocarpine hydrochloride may be used in a composition in ranges of 1% to 1.5% w/v, more preferably above 1% w/v and below 1.5% w/v, for example 1.16% w/v to 1.32% w/v, or 1.1875% w/v to 1.3125% w/v. Additional ranges of pilocarpine hydrochloride that may be used include 0.95% w/v to 1.2% w/v, 1.1% w/v to 1.4% w/v, and 1.2% w/v to 1.3% w/v. A preferred amount of pilocarpine hydrochloride is 1.25% w/v. Other amounts of pilocarpine hydrochloride that may be used include for example and without limitation, 0.5% w/v, 0.6% w/v, 0.7% w/v, 0.8% w/v, 0.9% w/v, 0.95% w/v, 0.99% w/v, 1% w/v, 1.01% w/v, 1.05% w/v, 1.08% w/v, 1.1% w/v, 1.15% w/v, 1.2% w/v, 1.21% w/v, 1.22% w/v, 1.23% w/v, 1.24% w/v, 1.26% w/v, 1.27% w/v, 1.28% w/v, 1.29% w/v, 1.3% w/v, 1.31% w/v, 1.32% w/v, 1.35% w/v, 1.4% w/v, 1.45% w/v, 1.49% w/v, and 1.5% w/v, and ranges and amounts between any of these selected amounts of pilocarpine hydrochloride. It will also be understood that in some embodiments involving non-hydrochloride salts of pilocarpine, corresponding molar equivalent amounts of these other salts can be used. For example, a 1.25% w/v pilocarpine hydrochloride composition (molecular weight of 244.72 g/mol) would be equivalent to a composition of 1.06% w/v pilocarpine when the weight of the hydrochloride is subtracted. A corresponding molar equivalent amount of the pilocarpine nitrate salt (molecular weight of 270.527 g/mol) would therefore have a concentration of 1.38% w/v. Similar molar conversion calculations may be made for other amounts and ranges disclosed herein.

In the embodiments described herein, compositions may be administered once daily, twice daily, or more. Preferably, the compositions are administered once daily. When administered, the compositions preferably have a duration of action sufficient for an entire day. In some embodiments, the compositions may have a duration of effect of at least two hours, at least three hours, preferably at least four hours, more preferably at least six hours, more preferably at least eight hours, even more preferably at least 10 hours, as well as all intervening time points. Some embodiments may provide for a composition having a duration of action greater than 10 hours, for example 12 hours, or even 24 hours. The duration of action refers to the duration of time that the administered composition has an effect on at least one vision parameter or ocular condition (e.g., presbyopia).

In some embodiments, when pilocarpine is part of a composition, the compound is the sole active ingredient which has therapeutic activity for the treatment of an ocular condition or for improving a vision parameter. The term "active ingredient" as used herein refers to a component of a composition which is responsible for the therapeutic effect of composition, whereas the other components of the composition (e.g. excipients, carriers, and diluents) are not responsible for the therapeutic effect of composition, even if they have other functions in the composition which are necessary or desired as part of the formulation (such as lubrication, pH control, emulsification, stabilization, preservation, and other functions other than the effect of composition as described herein). In some embodiments, compositions described herein in which pilocarpine is the sole active ingredient which has therapeutic activity are compositions in which there are no other components which would be considered to have therapeutic activity for the treatment of ocular conditions or improvement of vision parameters.

The compositions described herein may comprise a suitable preservative. Examples of suitable preservatives include benzalkonium chloride ("BAK"), Polyquaternium-1 (Polyquad®), chlorobutanol, stabilized chlorine dioxide, and others. Stabilized chlorine dioxide, also known as Purite®, may be described as an aqueous solution of sodium chlorite ($NaClO_2$). U.S. Pat. No. 5,424,078, which is incorporated herein by reference in its entirety, further discusses the use of stabilized chlorine dioxide as a preservative for ophthalmic formulations.

Topical cholinergic agonists act on the ciliary muscle, located in the ciliary body of the eye, and which is one of the richest areas of cholinergic receptors in the central nervous system. Pilocarpine also acts on the muscarinic cholinergic receptors found on the iris sphincter muscle, causing the muscle to contract, resulting in pupil constriction (i.e., miosis) (Levin et al., Adler's Physiology of the Eye, $11^{th}$ edition by Saunders Elsevier (Edinburgh), pp. 56, 57, and 509-510).

When topical pilocarpine is applied to the eye, the cholinergic receptors are activated in the ciliary muscle, thereby causing it to contract, which in turn opens the trabecular meshwork (Id, pp. 44, 45, and 289-291). This can facilitate the rate at which aqueous humor leaves the eye and the net result is a reduction of the intraocular pressure ("IOP") in patients with primary open angle glaucoma. Pilocarpine, with stimulation of the ciliary muscle, can cause a forward movement of the ciliary body with ciliary muscle contraction, relaxation of the zonules causing the central surfaces of the crystalline lens to steepen, and the central thickness of the lens to increase (anterior-posterior diameter) (Id, pp. 44-55). The net result is an increase in the diopter power of the lens which can lead to a number of patient complaints, including reduced visual acuity at near and far distances and ocular discomfort with higher concentrations of pilocarpine instilled in the eye. These adverse effects on the vision have been demonstrated in a number of clinical trials (Brown et al., Arch Ophthalmol. 94, pp. 1716-1719, 1976, and Diestelhorst M, "The additive intraocular pressure-lowering effect of latanoprost 0.005% daily once and pilocarpine 2% t.i.d. in patients with open-angle glaucoma or ocular hypertension. a 6-month, randomized, multicenter study. German Latanoprost Study Group," Graefes Arch Clin. Exp. Ophthalmol., 238(5), pp. 433-439). These adverse effects are also listed in the Isoptocarpine product label (See IsoptoCarpine® label approved on Jun. 22, 2010, page 6).

At the peak of topical cholinergic agonist use in clinical practice in the 1970s, different topical ophthalmic medications were manufactured in a wide range of concentrations to be able to meet individual patient needs for lowering IOP to treat glaucoma. Pilocarpine (IsoptoCarpine, Alcon) had 0.25%, 0.5%, 1.0%, 2.0%, 3.0%, 4.0%, 5.0%, 6.0%, 8.0%, and 10.0% (w/v) concentrations available at frequent QID (4 times daily) dosing to have a sustained effect since the drug has a short half-life in the aqueous humor (Id). Clinical trials have also demonstrated that QID dosing with pilocarpine is more effective than BID (twice daily) dosing in lowering IOP (Quigley et al., Ann. Ophthalmol. 9, pp. 427-430, 1977 and Harbin et al., Ann. Ophthalmol., 10, pp. 59-61, 1978). Clinical trials have also shown that higher concentrations, such as pilocarpine 4%, are more effective in lowering IOP than lower concentrations (e.g., <4%) (Boger et al., Am. J. Ophthalmol. 86, pp. 8-18, 1978). One study compared three concentrations of pilocarpine used for 1-week treatment of patients with glaucoma, and results showed a mean percent fall in IOP from baseline of 17.5%, 26.8%, and 29.1% with the 1%, 4%, and 8% dose strengths, respectively (Harris et al., Am. J. Ophthalmol., 72, pp. 923-925, 1971).

Consequently, glaucoma management with pilocarpine typically begins with lower concentrations, with the dose strengths being individually titrated upwards so as to permit patients to achieve target IOP sufficient to prevent further visual field deterioration (Ritch et al., The Glaucomas, Mosby (St. Louis), p. 516, 1989 and Kini et al., Arch Ophthalmol., 89, pp. 190-192, 1973). This is also true for cholinergic glaucoma medications other than pilocarpine, where the eye care provider initiates topical drug therapy with a low concentration and increases the dose strengths as needed to achieve a patient's target IOP (Phillips et al., Trans Ophthalmol. Soc. U.K., 86, pp. 233-245, 1966). Thus, it is commonly understood that pilocarpine has an upwardly sloping dose response curve.

However, escalating doses of pilocarpine in order to retain adequate IOP control often increases dose-dependent adverse events. For example, blurry vision at near and far distances is a common side effect of commercial pilocarpine formulations. The prescribing information for Isoptocarpine notes that a common adverse reaction is blurred vision; additional potential visual disturbances noted in the label include accommodative change and "visual impairment (dim, dark, or 'jumping' vision)". The prescribing information warns patients to exercise caution in night driving or other situations with poor illumination, and, recognizing the risk of blurry vision, warn against driving or using machinery if the patient's vision is not clear.

In patients approximately 40 years old or greater, there is a gradual loss in the ability to focus (particularly at close distance) primarily due to stiffening of the lens in the eye, a refractive condition known as presbyopia (Levin et al., Adler's Physiology of the Eye E-Book, $11^{th}$ edition by Saunders Elsevier (Edinburgh), pp. 59-61). It has been suggested that, following topical application of pilocarpine, the increase in accommodation from the ciliary muscle contraction and/or the miosis can create a "pin-hole effect" that may potentially improve the near and intermediate vision in some patients by increasing the depth of field, although the most effective dosing frequency and dose concentrations have not been defined. Some teachings have also advocated combining pilocarpine with other active ingredients, such as alpha-2 adrenergic receptor agonists. However, such combinations may implicate additional side effects on top of those related to pilocarpine. For example, common oxymetazoline side effects include ocular burning and stinging, blurry vision, watery eyes, headache, dizziness, and nervousness.

Commercial preparations of pilocarpine for glaucoma are typically formulated with viscosity enhancers which include hydroxypropyl methylcellulose, povidone, and carbopol 940 (Ritch et al., The Glaucomas, Mosby (St. Louis), p. 517, 1989). Viscosity enhancing polymers are commonly used in topical ophthalmic preparations to reduce the clearance of pilocarpine through lacrimal drainage so as to increase the residency time of the drug on the cornea, thereby increasing bioavailability and IOP effect (Reddy, Ocular Therapeutics and Drug Delivery: A Multi-Disciplinary Approach, Technomic Publishing AG (Lancaster), pp. 387-389, 1996). Polymers may also be used as demulcents to increase the comfort of ophthalmic preparations once placed upon the eye, and are typically described as having a lubricant and/or soothing effect (Abelson et. al., Demystifying Demulcents, Review of Ophthalmology, 2006).

Unfortunately, the viscosity due to added polymers in such ophthalmic formulations can result in adverse effects such as vision blur that limit their use (Hall et al., *Optom. Vis. Sci.,* 88, pp. 872-880, 2011). Accordingly, adding (or increasing) polymer content and viscosity of an ophthalmic formulations may result in vision blur (Id).

The current use of pilocarpine ophthalmic solution in the ophthalmic context is limited by several commonly-experienced adverse events, including temporal and periorbital headache (i.e., brow ache), which may be due at least in part to rapid ciliary muscle contraction. Dosing frequencies and concentrations of pilocarpine, preferably as a monotherapy, that can effectively treat presbyopia without causing intolerable side effects such as severe headache and visual disturbances are therefore desired. Such embodiments have been discovered and are described in greater detail below.

Summary of Clinical Studies

Clinical Study A

The safety and efficacy of pilocarpine hydrochloride 1% w/v ophthalmic solution alone was evaluated in one arm of a multicenter, double-masked, randomized, vehicle-controlled study in patients with presbyopia in a clinical study. The clinical study is referred to herein as Clinical Study A and is summarized in Example 1, and involved once or twice daily pilocarpine administration, each over a 3-day study period.

Unexpectedly, pilocarpine provided a greater improvement on reading ability with QD (once daily) dosing compared with BID (twice daily) dosing. The percentage of patients achieving a clinically relevant 2-line (10 letter) improvement from baseline in Uncorrected Near Visual Acuity (UNVA) at the majority of time points measured over an 8-hour period each day over the study period was 70.6% in the QD dosing group compared with 56.3% in the BID dosing group.

Clinical Study B

Following the results of Clinical Study A, an additional clinical study, referred to as Clinical Study B and described in Example 2, was performed to examine the effects of multiple dose concentrations of pilocarpine in patients with presbyopia using the QD dosing frequency that appeared to be better than BID from the aforementioned Clinical Study A.

As detailed in Example 2, a multicenter, double-masked, randomized, vehicle-controlled clinical study in 160 patients with presbyopia was performed. This clinical study included arms receiving pilocarpine hydrochloride 0.5%, 1%, and 1.5% w/v with QD dosing over a 2-day study period. Additional arms also tested the effect of combining pilocarpine with varying concentrations of oxymetazoline. Uncorrected near vision was measured each day at 1, 3, 6, 8, and 10-hours post pilocarpine administration.

Unexpectedly, the average letter change from baseline over the 2-day study period was numerically higher in the pilocarpine 1% group vs the 1.5% group (FIG. 1). The percentage of patients achieving a clinically relevant 2-line (10 letter) improvement of uncorrected near visual acuity at the majority of time points measured over a 10-hour period each day over the study period was 23.8% in the 1% dosing group vs. 22.2% in the 1.5% QD dosing group.

Figure 2:
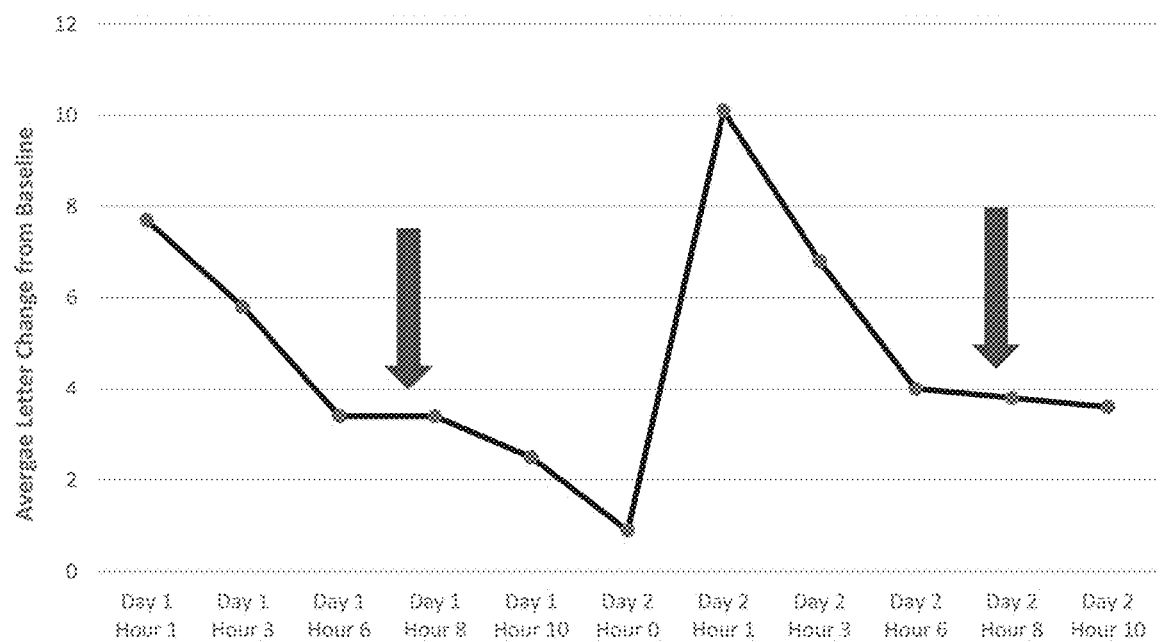
FIG. 2 shows the average change from baseline of UNVA at each timepoint over a two-day dosing period in the pilocarpine 1% Group, where one drop of pilocarpine hydrochloride was administered at Hour 0 on Day 1 and Day 2. (mITT, non-dominant eye, Clinical Study B).

In addition, there was an unexpected sustained plateau effect between 6 and 10 hours with pilocarpine 1% on improved reading ability in terms of average letter change from baseline (FIG. 2). This "plateau effect" (see arrows in Figure) was not predicted from previous non-clinical ocular pharmacokinetics studies, where pilocarpine levels in the ciliary muscle tissues rapidly diminish over time and a sustained improvement at the later time points would therefore not be expected. The previous study (Clinical Study A) also confirmed a sustained vision improvement at the later hours of measurement after day 1.

Figure 4:
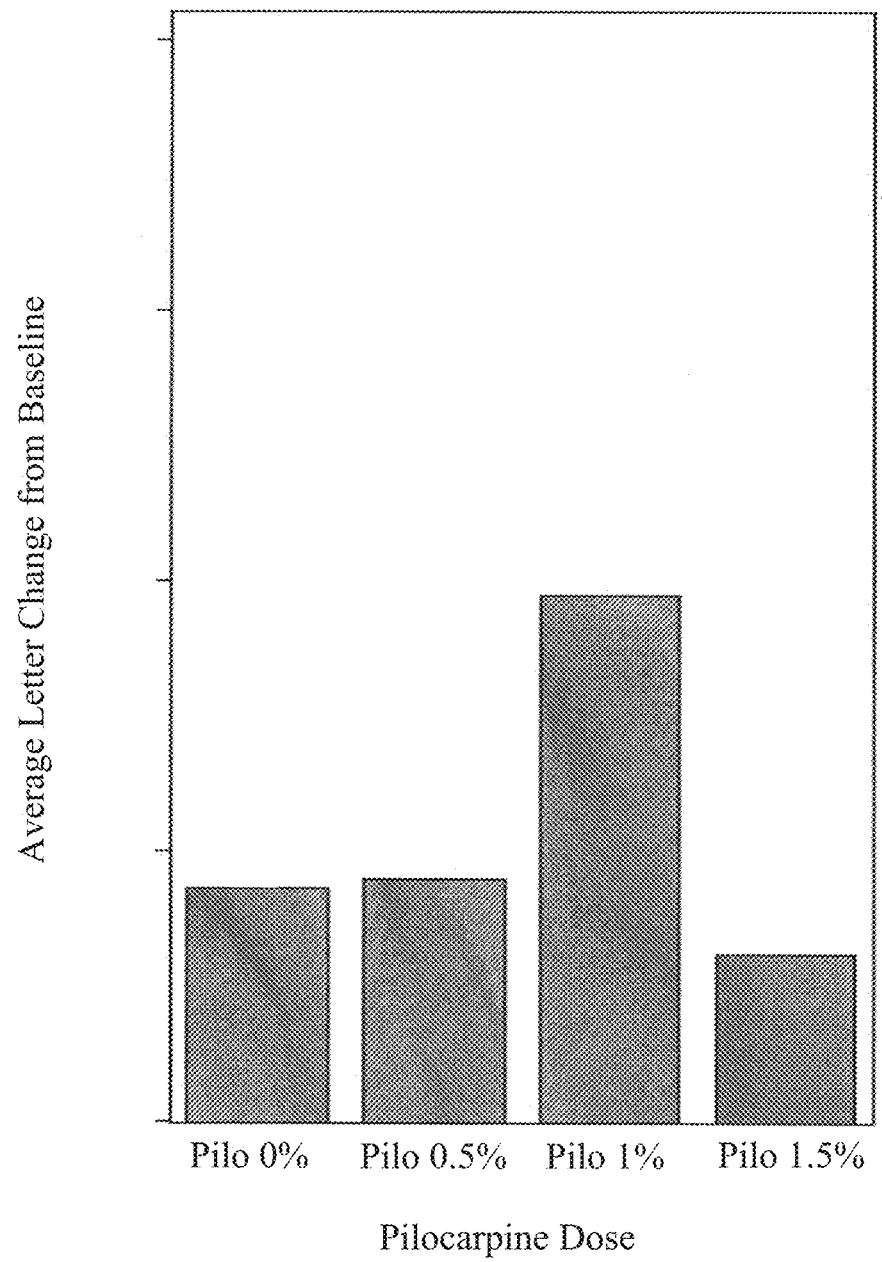
FIG. 4 shows the average letter change from baseline of UDVA over a 2-day dosing period in clinical study B.

In the instant clinical studies, such as Clinical Study B (and as described in greater detail below), the distance vision was measured at 1, 3, 6, 8, and 10-hours post pilocarpine administration with QD dose strength of 0.0% (control), 0.5%, 1%, and 1.5% over 2 days. The purpose of measuring distance vision is that pilocarpine frequently leads to a reduction of visual acuity at far distances, with patients complaining of blurry vision (Brown et al., *Arch Ophthalmol.*, 94, pp. 1716-1719). Unexpectedly, an improvement in distance visual acuity from baseline over the control arm was observed, most consistent with a pilocarpine concentration of 1%. (FIG. 4). At the 11 time points measured after QD dosing over the 2-day study, the pilocarpine 1% dose had numerically higher distance vision improvement at 9-time points vs control, as reflected, for example, in the average letter change from baseline. In addition, the distance vision improvement with pilocarpine 1% was numerically higher than 1.5% at all 11 time points, as reflected, for example, in the average letter change from baseline. Patients receiving pilocarpine 1.5% experienced a reduction in the mean distance visual acuity from baseline at 2 of these time points. In addition to the improved efficacy, ocular adverse effects were lower with the pilocarpine 1% dose strength versus the 1.5% dose strength.

Figure 7:
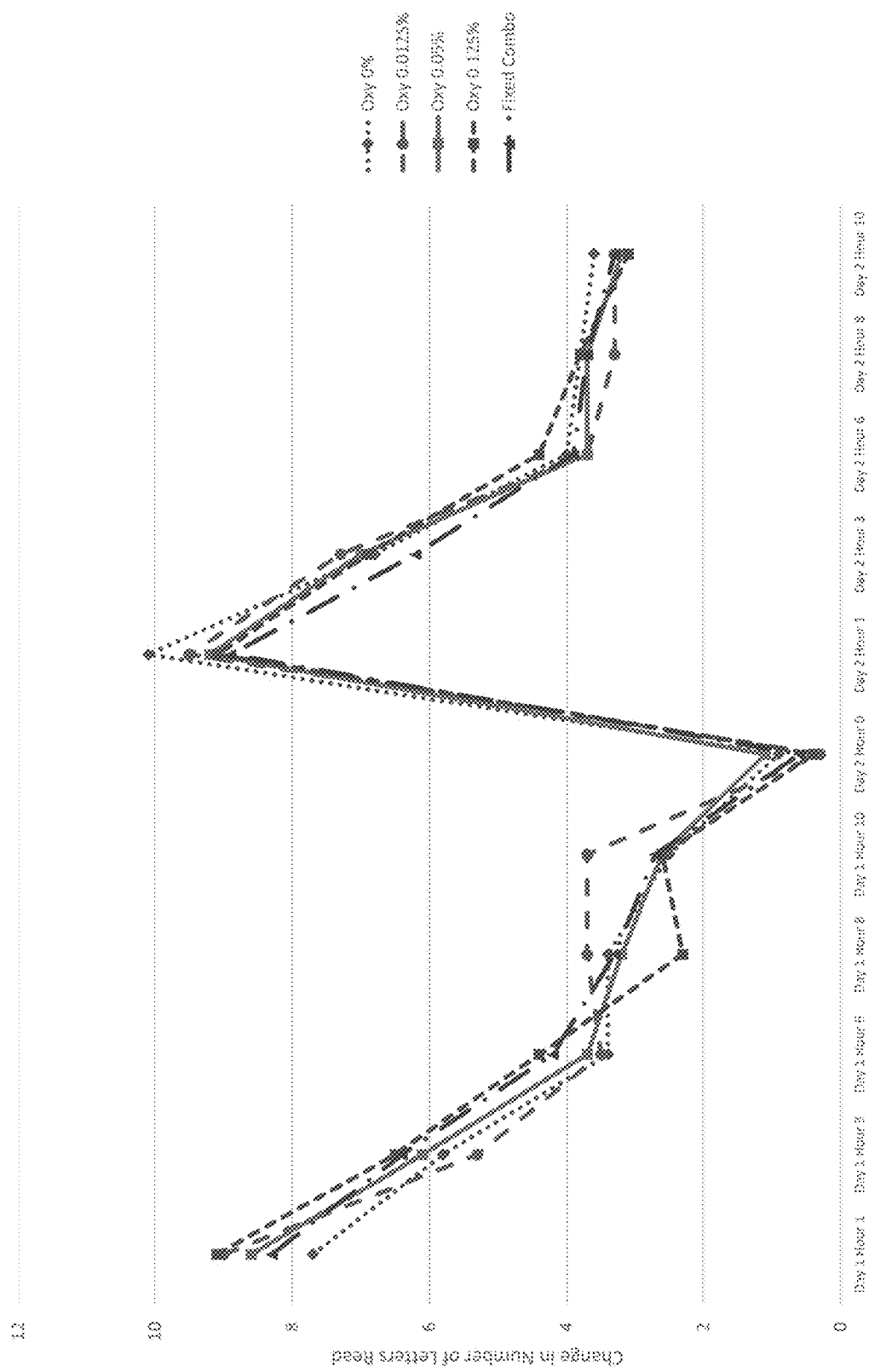
FIG. 7 illustrates a comparison of the change in UNVA number of letters read by timepoint following 1% pilocarpine administration with different concentrations of oxymetazoline.

Surprisingly, the clinical studies also showed that the tested pilocarpine compositions, when administered in combination with oxymetazoline hydrochloride at 0%, 0.0125%, 0.05%, and 0.125% w/v, did not show any significant additional effect or reduction of adverse events. It had been expected that the addition of oxymetazoline to pilocarpine would extend the duration of effect or increase the magnitude of effect on vision. As shown in FIG. 7, there was no meaningful difference between groups where pilocarpine was tested alone, and those where pilocarpine was administered together with oxymetazoline. Similarly, oxymetazoline did not reduce the incidence of adverse events. As a result, the findings from the clinical study surprisingly indicated that pilocarpine would perform well as a sole active ingredient, opposing the expectation that it would perform better in combination with another active such as oxymetazoline.

The clinical studies suggest that the dosing frequency and concentrations of pilocarpine to achieve optimal reading efficacy is contrary to the conventional use of pilocarpine for lowering IOP. When pilocarpine is used for lowering IOP, a linear relationship exists and increasing pilocarpine concentrations and dosing frequency leads to greater IOP reduction. Here, however, clinical studies indicate that QD pilocarpine dosing with concentrations ≥1% and <1.5% are most effective for improving reading abilities in patients with presbyopia. The mechanism for this is, however, not known.

To identify the optimal dose strength of pilocarpine to treat ocular conditions and/or improve vision parameters while minimizing adverse events, computational modeling was performed. Computational modeling is a validated approach using existing clinical data that the U.S. Food and Drug Administration advocates to identify best doses and clinical trial scenarios to accelerate drug development and has been used successfully in real practice (see, e.g., Challenge and Opportunity on the Critical Path to New Medical Products, FDA, 2004, Page 24).

Figure 3:
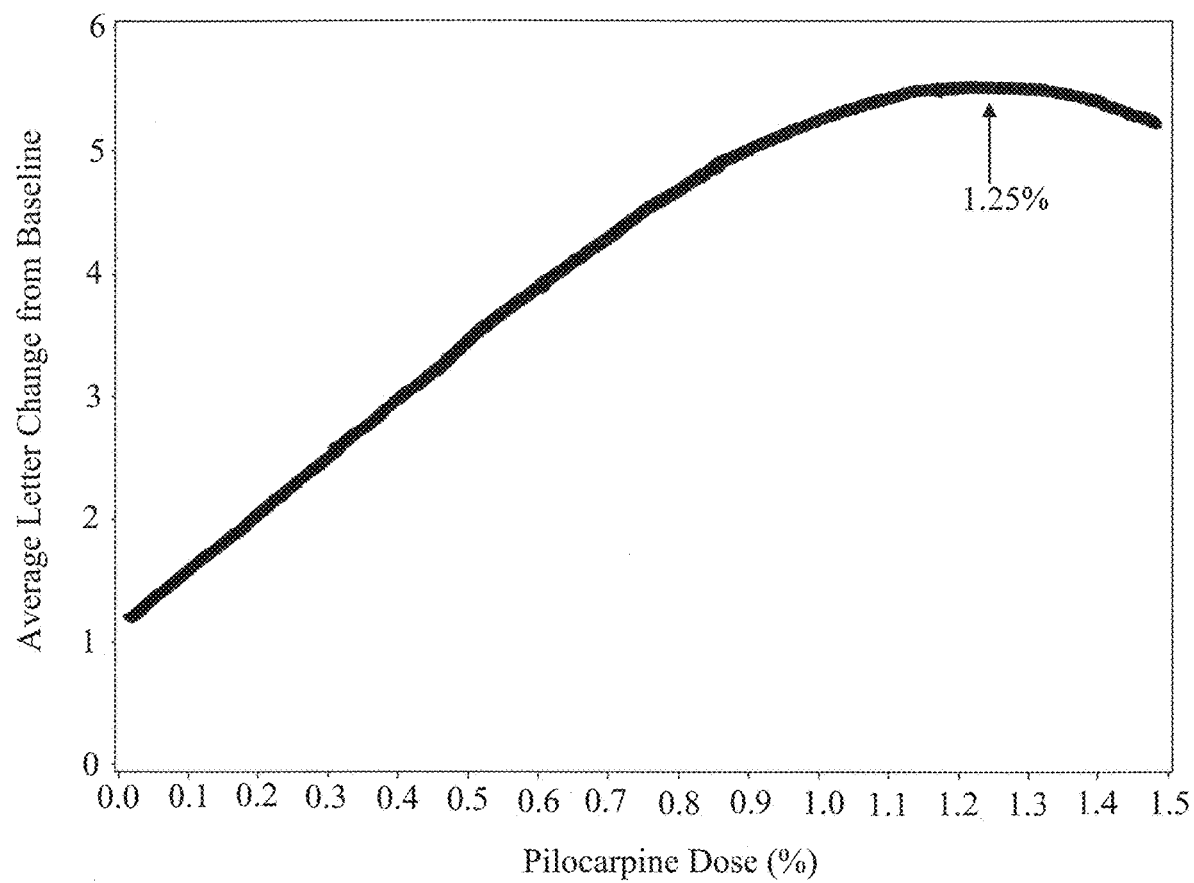
FIG. 3 illustrates a model of the most effective pilocarpine concentration range for improving near vision.

A polynomial regression model based on data from clinical studies was developed with the covariates that included linear, quadratic and cubic pilocarpine doses, baseline mesopic UNVA severity and iris color. Results (FIG. 3) showed that the most effective pilocarpine dose strength that can achieve the low bound of 5.5 mesopic near vision letter improvement is between 1.16% and 1.32% (Mid-Point=1.25%).

Figure 5:
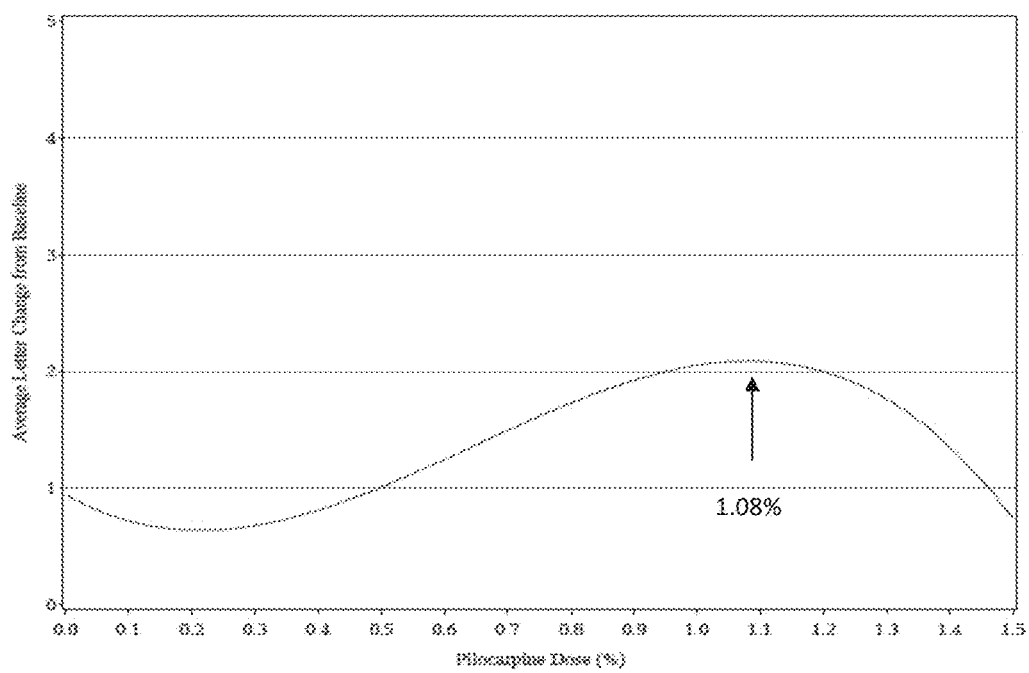
FIG. 5 illustrates a computational model of the most effective pilocarpine concentration range for improving distance vision.

Since the relationship of distance visual improvement and pilocarpine dose strength was non-linear, computational modeling was performed to identify the most effective dose strength for distance vision improvement using the similar polynomial regression model described above. Results (FIG. 5) showed that the most effective pilocarpine dose strength that can achieve the low bound of 2.0 mesopic distance vision improvement is between 0.95% and 1.2% (Mid-Point=1.08%).

Based at least in part upon these findings, further testing was conducted using a 1.25% w/v pilocarpine hydrochloride formulation. As described, for example, in Clinical Studies C and D (Examples 6 and 7 below), such a formulation is believed to provide maximal near vision improvements, while maintaining distance visual acuity, and further while minimizing ocular adverse events. Of course, other ranges and amounts of pilocarpine may be used, as noted previously.

Contrary to the prevailing use of pilocarpine hydrochloride, the pilocarpine formulations used in the clinical studies described herein comprised no polymers, thereby limiting the potential for vision blur. Since viscosity is a surrogate for the blur potential of an ophthalmic formulation, the viscosity of an embodiment of a polymer-free pilocarpine formulation was compared to viscosity of commercially available polymer-containing pilocarpine formulation (Isoptocarpine, which contains hydroxy propyl methyl cellulose), as described in Example 4. Results showed that with equal drug concentrations of 1% pilocarpine, commercial polymer-containing formulations were approximately 20-fold more viscous than the polymer-free formulations described herein. These polymer-free formulations were close to the viscosity of water (i.e., 1 centipoise), and are therefore not likely to result in vision blur. By contrast, the more viscous commercial formulations are likely to cause significant vision blur when dosed on a patient's eye, given its high viscosity.

Traditional pilocarpine usage in glaucoma requires an increase in dose strength (with formulations of up to 10% pilocarpine) and an increase in dosing frequency (up to four times daily) in order to provide adequate IOP reduction and control. Moreover, pilocarpine has been found to adversely affect vision (at both near and far distances), and is also tied to more serious adverse events (such as headache) when used at the higher drug concentrations and dosing frequencies typically used for treating glaucoma.

Surprisingly, however, the inventors have discovered that a pilocarpine concentration ≥1% and ≤1.5% (preferably about 1.25%) improves vision at both near and far distances while causing minimal adverse events (e.g., brow ache, headache). While the removal of polymers was expected to have reduced the residence time of pilocarpine on the ocular surface and its subsequent effect, the polymer-free compositions described herein unexpectedly did not reduce pilocarpine's duration of effect—to the contrary, once-daily dosing was discovered to better maintain the visual improvement over a 10-hour period than more frequent dosing (e.g., twice-daily administration). The removal of polymers also reduced the potential for vision blurring and other such issues. Also unexpectedly, and contrary to the prevailing use of pilocarpine hydrochloride, it was discovered that treatment of presbyopia with pilocarpine did not require an increasing dose to maintain a constant effect on vision improvement, and a steady-state dose of pilocarpine maintains a consistent effect on vision. At the same time, adverse events were surprisingly minimal when pilocarpine was administered as the sole active agent, and the addition of other active ingredients such as oxymetazoline did not demonstrate any meaningful improvement in the duration/magnitude of effect or the incidence of adverse events.

It is not known why, in comparison to the glaucoma treatment mechanism of action, these particular lower dose strengths and reduced dosing frequencies provide greater visual improvement. This discovery is contrary to the conventional use of pilocarpine for lowering IOP, which teaches that more frequent daily dosing (up to 4 times daily) and higher dose strengths (up to 10%) are most effective. Despite not having a polymer to increase drug residency in the tear film and improve bioavailability, once daily administration of the instant pilocarpine compositions described herein provided up to 10 hours or more of vision improvement.

The following examples are illustrative in nature and are in no way intended to be limiting.

Example 1

Clinical Study A and Analysis

Clinical Study A is a multicenter, double-masked, randomized, vehicle-controlled study which determined the effect of once- or twice-daily dosing of pilocarpine. Seventeen patients were treated with pilocarpine hydrochloride 1.0% w/v followed by vehicle in the non-dominant eye, and vehicle alone in the dominant eye. The respective formulations used are set forth in Table 4 below. One patient discontinued the study, due to a nonocular adverse event.

Figure 6:
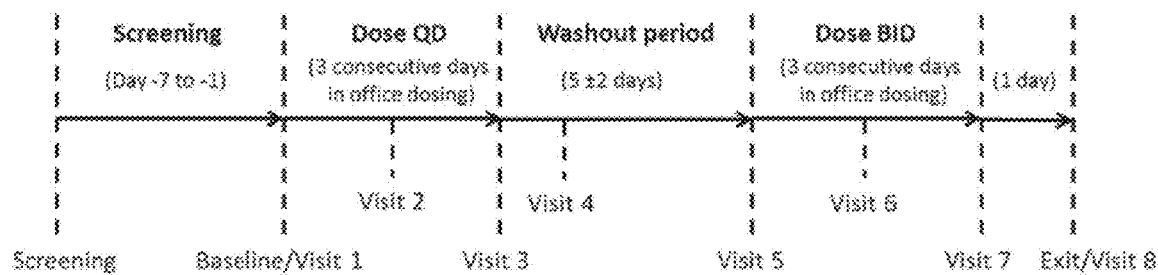
FIG. 6 shows the scheme of the study design in Clinical Study A.

Study medication was administered once daily (QD) in each eye during office visits 1 through 3 at hour 0 (8 AM±1 hour). Following a 5±2 day washout period, study medication was administered twice daily (BID) in each eye during office visits 5 through 7 at hour 0 (8 AM±1 hour) and hour 5 (5 hours±15 minutes after hour 0 dose administration). Patients returned on visit 8 for safety testing and exit from the study. The study design was illustrated in FIG. 6.

The primary efficacy variable was UNVA response at visit 3. A UNVA responder was defined as a patient with at least a 2-line improvement in mesopic, high contrast UNVA in the non-dominant eye from baseline (hour 0 of visit 1) at a majority (at least 3) of time points post dose.

During the QD dosing period, the percentage of patients achieving the primary endpoint, at least a 2-line improvement from baseline in mesopic, high contrast UNVA (hour 0 of visit 1) in the non-dominant eye at a majority (at least 3) of time points post dose was 70.6%. These patients also showed statistically significant superiority (p=0.020 to 0.058) for the nondominant eye (active) over the dominant eye (vehicle) in the percent of patients achieving a 2-line improvement in mesopic, high contrast UNVA from baseline at a majority of timepoints postdose from visits 2 to 7.

During the BID dosing period, the percentage of patients achieving the primary endpoint, at least a 2-line improvement from baseline in mesopic, high contrast UNVA (hour 0 of visit 5) in the non-dominant eye at a majority (at least 3) of time points post dose was 56.3% (p=0.035 to 0.058).

It was unexpected that the pilocarpine provided more improvement on reading ability with QD (once daily) dosing compared with BID (twice daily) dosing.

Example 2

Clinical Study B and Analysis

A multicenter, double-masked, parallel-group, randomized sequence, dose response, vehicle-controlled study in patients with presbyopia was conducted. Four treatment groups were defined based on the concentration of pilocarpine hydrochloride ophthalmic solution to which patients were randomly assigned (0%, 0.5%, 1%, or 1.5% w/v). Each dosing period lasted for two days. Although not the primary focus of this present discussion, each of the tested pilocarpine concentrations was paired with four different concentrations of oxymetazoline hydrochloride ophthalmic solution (0%, 0.0125%, 0.05%, or 0.125% w/v) administered as an unfixed combination, as well as a group which received a fixed combination of pilocarpine hydrochloride 1% w/v in combination with oxymetazoline hydrochloride 0.125% w/v.

Pilocarpine hydrochloride 0.5, 1, and 1.5% w/v ophthalmic solutions also contained benzalkonium chloride, boric acid, sodium citrate dihydrate, sodium chloride, hydrochloric acid/sodium hydroxide, and purified water, whereas pilocarpine hydrochloride 0% contained no pilocarpine or any salt thereof but only the excipients/carriers (i.e., benzalkonium chloride, boric acid, sodium citrate dihydrate, sodium chloride, hydrochloric acid/sodium hydroxide, and purified water).

Oxymetazoline hydrochloride ophthalmic solution 0.0125, 0.05, or 0.125% w/v contained oxymetazoline hydrochloride, benzalkonium chloride, boric acid, sodium citrate dihydrate, sodium chloride, hydrochloric acid/sodium hydroxide, and purified water, whereas oxymetazoline hydrochloride 0% contained no oxymetazoline or any salt thereof but only the excipients/carriers (i.e., benzalkonium chloride, boric acid, sodium citrate dihydrate, sodium chloride, hydrochloric acid/sodium hydroxide, and purified water).

Patient Eligibility

Enrollment of approximately 160 patients with presbyopia was planned (40 per pilocarpine group). A total of 157 patients were enrolled, treated, and included in the mITT population (40, 37, 42, and 38 in the pilocarpine hydrochloride 0%, 0.5%, 1%, and 1.5% groups, respectively). 161 patients were included in the safety populations (41, 39, 42, and 39 in the pilocarpine hydrochloride 0%, 0.5%, 1%, and 1.5% groups, respectively). All patients in the mITT and safety populations completed the study except for 2, 2, 1, and 3 patients in the pilocarpine 0%, 0.5%, 1%, and 1.5% groups, respectively, who discontinued early due to withdrawal of consent and loss to follow-up.

Following a screening visit (Days −18 to −1) patients were randomized at a baseline visit (Visit 1) in a 1:1:1:1 ratio (stratified by the UNVA at baseline of ≤20/80 and >20/80) to 1 of the 4 pilocarpine treatment groups. For each 2-day dosing period, active study treatments were administered once daily in the nondominant eye, and vehicle control treatments were administered once daily in the dominant eye.

Efficacy and Safety Measurements

Efficacy: The primary efficacy measure was mesopic (defined by lighting 3.2 to 3.5 candelas [cd]/m$^2$ [10 to 11 lux] measured at the target), high contrast UNVA in the non-dominant eye. The primary efficacy variable was the average letter change from baseline under the condition of mesopic, high contrast UNVA in the non-dominant eye. Baseline was the Day 1 Hour 0 measure for each dosing period. The primary efficacy endpoint was the average letter change from baseline under the condition of mesopic, high contrast UNVA in the nondominant eye over 2-day periods between Hour 1 and Hour 10.

Other efficacy measures were mesopic distance (4 meters) and near (40 mm) pupil diameter, mesopic distance and near target refraction (diopters [D], as measured by Grand Seiko autorefractor), and mesopic, high contrast UDVA.

Safety: Safety measures were adverse events (AEs), photopic high contrast UDVA, vital signs (blood pressure and heart rate), macroscopic hyperemia assessment, study drug tolerability and drop comfort assessments, temporal and supraorbital headache assessment, intraocular pressure (IOP), slit lamp biomicroscopy, dilated funduscopic examinations, and pregnancy tests for females of childbearing potential. In addition, the following safety measures were collected only at screening for determination of patient eligibility: Schirmer's tear test (with anesthesia), pupillary response assessment, photopic pupil measurement (both eyes; distance; measured with Grand Seiko), sodium fluorescein corneal staining (Oxford scale), cycloplegic refraction (photopic distance), and gonioscopy angle assessment.

Statistical Methods

Analysis Populations: The modified intent-to-treat (mITT) population was defined as all randomized patients with a baseline and at least 1 post baseline assessment of mesopic, high contrast, UNVA, and with a baseline UNVA that did not change by more than three lines over five dosing periods. The efficacy variables were analyzed using the mITT population on an as-randomized basis.

The safety population was defined as all patients who received at least one dose of study treatment. All safety measures were analyzed using the safety population on an as-treated basis.

Disposition and Demographics: Patient disposition was summarized for all screened patients and overall and by treatment group for the mITT population. Important protocol deviations were summarized for the mITT population. Demographic variables were summarized for all screened patients and overall and by treatment group for the mITT, PP and safety populations. Medical history and prior and concomitant medications were summarized overall and by treatment group for the safety population. The National Eye Institute Visual Function Questionnaire 25 (NEI VFQ-25), administered at screening, was summarized for the safety population.

A total of 163 patients were enrolled at 15 investigational sites and 157 patients were included in the mITT population (40, 37, 42, and 38 in the pilocarpine hydrochloride 0%, 0.5%, 1%, and 1.5% groups, respectively). The overall mean (range) age for the mITT populations was 46.8 (40 to 50) years, and the majority was female (69.4%, 109/157), white (79.0%, 124/157), and non-Hispanic (81.5%, 128/157). Race and race group varied significantly across treatment groups (p=0.0312 and p=0.0475, respectively); all other demographic characteristics were similar across treatment groups. A total of 161 patients were included in the safety populations (41, 39, 42, and 39 in the pilocarpine hydrochloride 0%, 0.5%, 1%, and 1.5% groups, respectively). The patient disposition is summarized below:

TABLE 1

|  | Pilo 0% (Group 1) | Pilo 0.5% (Group 2) | Pilo 1.0% (Group 3) | Pilo 1.5% (Group 4) | Total |
|---|---|---|---|---|---|
| Safety | 41 | 39 | 42 | 39 | 161 |
| mITT | 40 | 37 | 42 | 38 | 157 |
| Completed | 38 (95.0%) | 35 (94.6%) | 41 (97.6%) | 35 (92.1%) | 149 (94.9%) |
| Discontinued | 2 (5.0%) | 2 (5.4%) | 1 (2.4%) | 3 (7.9%) | 8 (5.1%) |

All patients in the mITT and safety populations completed the study except for 2, 2, 1, and 3 patients in the pilocarpine hydrochloride 0%, 0.5%, 1%, and 1.5% groups, respectively, who discontinued early due to withdrawal of consent and loss to follow-up. The demographic and baseline characteristics in the mITT is summarized below:

TABLE 2

|  | Pilo 0% (N = 40) | Pilo 0.5% (N = 37) | Pilo 1.0% (N = 42) | Pilo 1.5% (N = 38) | Total (N = 157) |
|---|---|---|---|---|---|
| Mean Age (SD) (years) | 46.6 (2.9) | 47.1 (2.6) | 46.8 (2.8) | 46.6 (2.2) | 46.8 (2.6) |
| % 40-47 years | 52.5% | 43.2% | 52.4% | 63.2% | 52.9% |
| Sex (% male) | 20.0% | 32.4% | 31.0% | 39.5% | 30.6% |
| Race |  |  |  |  |  |
| % White | 77.5% | 81.1% | 66.7% | 92.1% | 79.0% |
| % Black | 15.0% | 13.5% | 31.0% | 7.9% | 17.2% |
| % Asian | 7.5% | 0% | 0% | 0% | 1.9% |
| % Other | 0% | 5.4% | 2.4% | 0% | 1.9% |
| Baseline UNVA |  |  |  |  |  |
| % 20/40-20/80 | 65.0% | 70.3% | 66.7% | 68.4% | 67.5% |
| % 20/100 or worse | 35.0% | 29.7% | 33.339 | 31.6% | 32.5% |

Efficacy: To examine the primary efficacy variable, the average change from baseline in mesopic, high contrast UNVA letters in the nondominant eye between Hour 1 and Hour 10 during each 2-day dosing period was examined using mixed-effects model for repeated measures (MMRM) with response surface and analysis of covariance (ANCOVA) modeling techniques.

The following additional efficacy analyses using the primary efficacy measure were also performed:
the proportions of patients with at least 3 lines and 2 lines improvement from baseline in mesopic, high contrast UNVA at a majority of post dose time points (6 or more) in the non-dominant eye,
the proportions of patients with at least 1 line, 2 lines, and 3 lines improvement from baseline, and the proportions of patients classified as 20/40 or better, 20/32 or better, 20/25 or better, and 20/20 or better during the mesopic, high contrast UNVA evaluation in the nondominant eye and binocularly at each time point of each dosing period, and
changes from baseline in the number of lines and the number of correctly read letters during the mesopic, high contrast UNVA evaluation in the non-dominant eye and binocularly at each time point of each dosing period.

All "other efficacy" analyses were performed at each time point of each dosing period. Changes from baseline were summarized for mesopic, near and distance pupil diameter, and for mesopic, near and distance accommodation in sphere and cylinder. The proportions of patients with at least 1 line, 2 lines, and 3 lines of improvement from baseline, and the proportions of patients classified as 20/40 or better, 20/32 or better, 20/25 or better, and 20/20 or better during the mesopic, high contrast UDVA evaluation were calculated for the nondominant eye and binocularly.

Efficacy Results

A. Primary Efficacy Results:

To examine the primary efficacy variable, the average letter change from baseline in mesopic, high contrast UNVA in the nondominant eye between Hour 1 and Hour 10 during each 2-day dosing period, response surface and ANCOVA method analyses were performed.

mITT population: The primary efficacy endpoint was the average change from baseline in mesopic, high contrast UNVA letters in the nondominant eye between Hour 1 and Hour 10 during each 2-day dosing period in the mITT population.

Overall, the response surface method analysis revealed a significant dose response driven by the pilocarpine dose ($p<0.0001$ and 0.0029), which was particularly evident up to the 1% dose level. The average letter change from baseline across multiple postdose timepoints increased as pilocarpine dose levels increased, and an average improvement of approximately 5 letters was observed for both the pilocarpine hydrochloride 1% and 1.5% dose levels.

A graph of average letter change from baseline was also generated from the results calculated using ANCOVA. FIG. 1 illustrates the significant effect of pilocarpine hydrochloride dose on mesopic, high contrast UNVA letters correctly read with the non-dominant eye up to the 1% dose level, after which the effect stabilized. A significant dose response emerged that was driven by the pilocarpine dose ($p<0.0001$). As seen in the figure, the vehicle and 0.5% pilocarpine concentrations showed a relatively weaker effect on vision, with mean improvements from baseline of 1.12 and 3.40 letters, respectively. Surprisingly, 1% pilocarpine showed a numerically greater mean improvement from baseline of 5.25 letters versus the higher concentration of 1.5% pilocarpine, which had an improvement of 5.11 letters.

B. Additional Analyses Using the Primary Efficacy Measure

Responder Analyses: The proportions of patients in the mITT population with at least 3 lines and at least 2 lines improvement from baseline in mesopic, high contrast UNVA at a majority of post dose timepoints (6 or more) in the non-dominant eye were also calculated to further examine the primary efficacy measure.

In addition, the proportions of patients with 1 line, 2 lines, and 3 lines improvement from baseline and the proportions of patients classified as 20/40 or better, 20/32 or better, 20/25 or better, and 20/20 or better, during the mesopic, high contrast UNVA evaluation, were calculated by time point.

Table 3 shows the proportion of patients with at least 2 lines of improvement from baseline in mesopic, high contrast UNVA at a majority of postdose timepoints in the nondominant eye by treatment group. The proportion of responders increased with increasing pilocarpine hydrochloride dose up to the 1% dose level.

TABLE 3

Proportion of Responders with 2-Line Improvement in Mesopic, High Contrast Uncorrected Near Visual Acuity in the Nondominant Eye by Treatment Group (mITT Population)

|  | Pilo 0% | Pilo 0.5% | Pilo 1% | Pilo 1.5% |
|---|---|---|---|---|
| N | 39 | 37 | 42 | 36 |
| Number (%) of Responders | 1 (2.6) | 2 (5.4) | 10 (23.8) | 8 (22.2) |

The values at Day 1 Hour 0 at each dosing period were used as baseline. Responder was defined as a patient with at least a 2-line improvement in mesopic, high contrast UNVA from baseline at a majority of postdose timepoints (6 or more) in the nondominant eye.

As a whole, these responder analyses provided further support for a significant dose response for mesopic, high contrast UNVA driven by pilocarpine hydrochloride dose up to the 1% dose level. As a whole across most postdose timepoints, proportions of patients with 1, 2, and 3 lines of improvement from baseline in the nondominant eye increased as dose levels of pilocarpine hydrochloride increased up to 1%.

Figure 8:
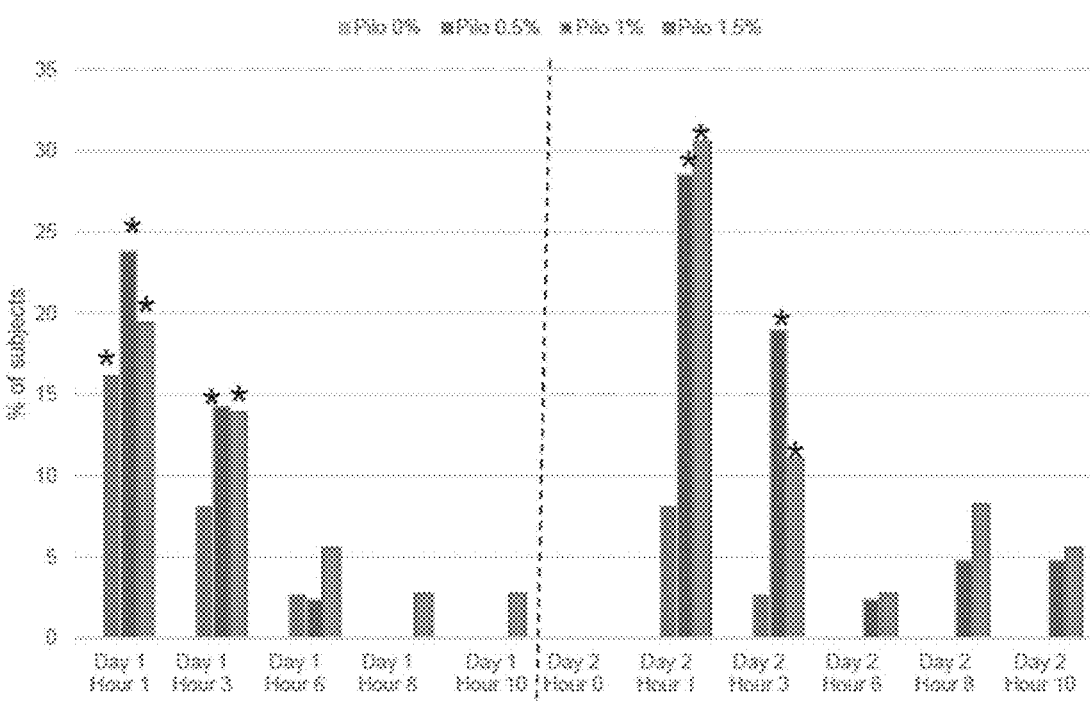
FIG. 8 shows a graph of 3-line improvement in mesopic UNVA (mITT population).
Figure 9:
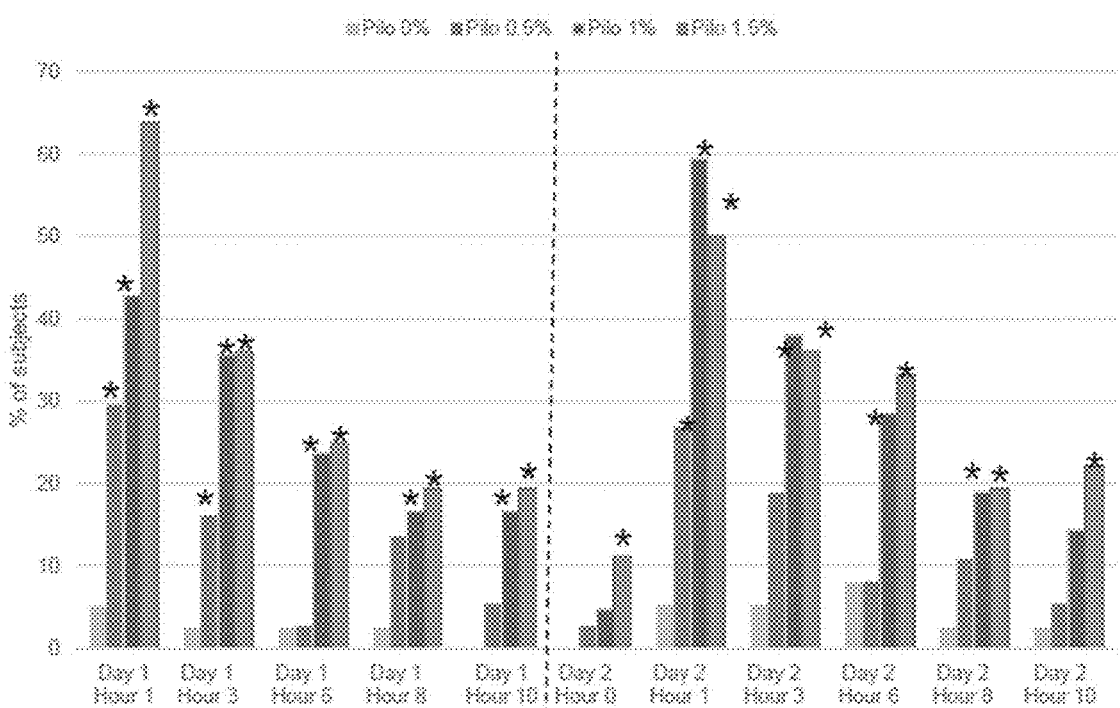
FIG. 9 shows a graph of 2-line improvement in mesopic UNVA (mITT population).

FIG. 8 and FIG. 9 show the proportion of responders with 3-line or 2-line improvement in mesopic UNVA (mITT population) at each time point for each tested group, respectively. At day 1, hour 1 in FIG. 8, the proportion of patients with a three line improvement in mesopic UNVA was 24% and 19% for pilocarpine hydrochloride 1% and 1.5%, respectively. At day 2, hour 1, the proportion of patients with a three line improvement in mesopic UNVA was 27% and 30% for pilocarpine hydrochloride 1% and 1.5%, respectively. With reference to FIG. 9, the proportion of patients with a two line improvement in mesopic UNVA at day 1, hour 1 was 43% and 64% for pilocarpine hydrochloride 1% and 1.5%, respectively. At day 2, hour 1, the proportion of patients with a two line improvement in mesopic UNVA was 60% and 50% for pilocarpine 1% and 1.5%, respectively.

Moreover, there was a statistically significant effect in 3 line improvement of mesopic, high contrast UNVA for pilocarpine hydrochloride 1% and 1.5% at both 1 and 3 hours post dosing on day 1 and day 2 in comparison to the vehicle. There was also a statistically significant effect in 2 line improvement of mesopic, high contrast UNVA for pilocarpine 1% and 1.5% at all time points post dosing on day 1 and day 2.

C. Other Efficacy Results

Mesopic, High Contrast Uncorrected Distance Visual Acuity

A similar analysis was performed during a mesopic, high contrast UDVA evaluation. FIG. 4 shows the average letter change from baseline under the condition of UDVA over a 2-day dosing period. While there were no significant effects on the change in UDVA from baseline for each treatment group, the average improvement in distance vision was numerically highest in the pilocarpine hydrochloride 1% group (mITT, non-dominant eye).

Safety Evaluation

The incidence of AEs with the vehicle (i.e. Pilo 0%) was similar to the AEs of the other pilocarpine groups. The lowest incidence of AEs was observed with the pilocarpine 1% group. There were no reports of burning or stinging and no unexpected safety findings were made. No patients were discontinued from the study due to an AE and no deaths occurred.

Oxymetazoline

FIG. 7 illustrates the change from baseline levels in letters read under UNVA mesopic conditions by timepoint, for 1% pilocarpine in combination with varying concentrations of oxymetazoline (0%, 0.0125%, 0.05%, 0.125% w/v, and in a fixed combination of 1% w/v pilocarpine hydrochloride and 0.125% w/v oxymetazoline hydrochloride). Similar results were seen for 1.5% pilocarpine in combination with oxymetazoline. With the exception of some minor timepoints, there was no significant difference in the duration of effect and change in letters read at a constant concentration of pilocarpine as the oxymetazoline concentration was varied. Moreover, there was no significant reduction in adverse events (e.g., headache) with the addition of oxymetazoline.

These results were surprising and unexpected, since it was thought that the coadministration of oxymetazoline and pilocarpine (in either a fixed or unfixed combination) would have either extended the duration and/or magnitude of effect, or else reduced the incidence of side effects. Instead, no such results were seen, and pilocarpine monotherapy (i.e., where pilocarpine is the sole active ingredient) was found to be as effective as pilocarpine coadministered with oxymetazoline.

Example 3

Several compositions were prepared with the ingredients as set forth below:

TABLE 4

| | Formulation No: | | | | |
|---|---|---|---|---|---|
| Ingredient (% w/v)[1] | 1 | 2 | 3 | 4 | 5 |
| Pilocarpine HCl | 0.00 | 0.5 | 1.0 | 1.25 | 1.5 |
| Benzalkonium chloride | 0.0075 | 0.0075 | 0.0075 | 0.0075 | 0.0075 |
| Boric acid | 1.0 | 1.0 | 1.0 | 1.0 | 1.0 |
| Sodium citrate dihydrate | 0.015 | 0.015 | 0.015 | 0.015 | 0.015 |

TABLE 4-continued

| Ingredient (% w/v)[1] | Formulation No: | | | | |
|---|---|---|---|---|---|
| | 1 | 2 | 3 | 4 | 5 |
| Sodium chloride | 0.37 | 0.26 | 0.14 | 0.08 | 0.03 |
| Hydrochloric acid and/or Sodium hydroxide | pH 3.0-5.5 | pH 3.0-5.5 | pH 3.0-5.5 | pH 3.0-5.5 | pH 3.0-5.5 |
| Purified water | QS | QS | QS | QS | QS |

[1]The density of formulations 1-5 are within 0.99-1.00 g/mL at 25.00° C. Hence, the composition ingredients in % w/v is equivalent to the % w/w.

In the table above, the pH range may be from 3.0 to 5.5. In a preferred embodiment, the target pH is 5.0.

Example 4

In Vitro Viscosity Testing

A study was conducted to compare the presence or absence of polymers on the viscosity of pilocarpine formulations. Currently available commercial pilocarpine formulations often contain viscosity-enhancing polymers serving to enhance the residence time of the formulation on the surface of the eye. For example, pilocarpine formulations developed by Alcon under the label "Isoptocarpine" contain hypromellose 2910 (also referred to as hydroxy propyl methyl cellulose). This same polymer is also found in other generic pilocarpine formulations (for example as currently sold by Akorn, Bausch & Lomb, and Sandoz).

Two formulations from Example 3 above (Formulations 3 and 4, containing 1% and 1.25% pilocarpine hydrochloride, respectively) were tested, together with three Isoptocarpine formulations with 1%, 2%, and 4% pilocarpine hydrochloride, as well as three generic pilocarpine formulations manufactured by Sandoz (also at 1%, 2%, and 4%). Viscosity testing was performed in accordance with USP <912> using a rotational viscometer. The three Isoptocarpine formulations were measured using an S18 spindle with a rotation speed of 60 rpm. The polymer-free Formulations 3 and 4 in accordance with the instant application were measured using an ultra-low viscosity spindle (00) with a rotation speed of 100 rpm. A calibration check was performed on the viscometer prior to analysis, and passed all requirements listed in the compendial chapter.

TABLE 5

Viscosity of Polymer-Free Pilocarpine Formulations Compared to Commercial Pilocarpine Formulations

| | IsoptoCarpine (Alcon) commercial formulations | | | Sandoz generic commercial formulations | | | Formulation 3 | Formulation 4 |
|---|---|---|---|---|---|---|---|---|
| Pilocarpine (% w/v) | 1% | 2% | 4% | 1% | 2% | 4% | 1% | 1.25% |
| Viscosity (cps) | 21 | 22 | 23 | 19 | 23 | 23 | 1 | 1 |

As described in Table 5 above, the polymer-free Formulations 3 and 4 had identical viscosities of 1 centipoise (cps). In contrast, the Isoptocarpine formulations showed much higher viscosities ranging from 21-23 cps. Similarly, the Sandoz generic pilocarpine formulations also showed higher viscosities ranging from 19-23 cps. At equal drug concentrations of 1% pilocarpine, the commercial formulations were approximately 20-fold more viscous than the polymer-free Formulation 4. This higher viscosity, due to the presence of polymers in the formulation, is believed to cause greater vision blurring when administered to the eye. By contrast, Formulation 4, which has a viscosity close to that of pure water (1 cps), is not likely to lead to significant vision blur. Accordingly, polymer-free pilocarpine formulations should cause substantially lower vision blurring or other vision impairments, especially when initially administered.

Example 5

In Vivo Testing

The ocular safety and tolerability of pilocarpine compositions was evaluated in a rabbit model. Specifically, Formulations 1 and 4 from Example 3 above were administered to two groups of five female albino New Zealand white rabbits. In Group 1, one drop (~35 µL) of Formulation 1 (vehicle) as referred to in Table 4 was administered to the left eye ("OS") once daily, with nothing administered to the right eye ("OD"). In Group 2, Formulation 4 (1.25% pilocarpine) as referred to in Table 4 was administered in a similar manner. All animals were treated in accordance with all requirements of the Guide for the Care and Use of Laboratory Animals and the United States Department of Agriculture (USDA), and all regulations issued by the USDA implementing the Animal Welfare Act, 9 CFR, Parts 1, 2, and 3. Rabbit pupil diameter and gross ocular observations were compiled.

The pupil diameter measurements and ocular observation scales are listed below:

Ocular Discomfort Description

| Score | Description |
|---|---|
| 0 | None: no consistent blinking or squinting. Some blinking may be seen as an adjustment to drop placement |
| +1 | Minimal: intermittent blinking |
| +2 | Mild: repeated blinking and/or squinting; partial closure of the eye may be observed |
| +3 | Moderate: repeated blinking and/or squinting with complete closure of the eye |
| +4 | Severe: firm closure of the eye for prolonged interval with pawing or rubbing is noted |

Ocular Discomfort Duration

| Score | Description |
|---|---|
| +1 | One to 30 seconds. |
| +2 | Thirty-one seconds to 60 seconds (one minute). |
| +3 | Sixty-one seconds to 120 seconds (two minutes). |
| +4 | One hundred twenty-one seconds and greater. |

Hyperemia

| Score | Description |
|---|---|
| 0 | Normal: may appear blanched to reddish pink without perilimbal injection (except at 12 and 6 o'clock positions) with vessels of the palpebral and bulbar conjunctiva easily observed |
| +1 | Mild: a flushed, reddish color predominantly confined to the palpebral conjunctiva with some perilimbal injection but primarily confined to the lower and upper parts of the eye from the 4 and 7 o'clock and the 11 and 1 o'clock positions |
| +2 | Moderate: bright crimson red color of the palpebral conjunctiva with accompanying perilimbal injection covering at least 75% of the circumference of the perilimbal region. Individual vessels are not easily discernable |
| +3 | Severe: dark, beefy red color with congestion of both the bulbar and the palpebral conjunctiva along with pronounced perilimbal injection. Petechiae may be present on the nictitating membrane and/or the upper palpebral conjunctiva |

Swelling

| Score | Description |
|---|---|
| 0 | Normal: no swelling of the conjunctival tissue |
| +1 | Minimal: swelling above normal without eversion of the lids (can be easily ascertained by noting that the upper and lower eyelids are positioned as in the normal eye); swelling generally starts in the lower cul-de-sac near the inner canthus |
| +2 | Mild: swelling with misalignment of the normal approximation of the lower and upper eyelids; primarily confined to the upper eyelid so that in the initial stages the misapproximation of the eyelids begins by partial eversion of the upper eyelid. In this stage, swelling is confined generally to the upper eyelid, although it exists in the lower cul-de-sac |
| +3 | Moderate: swelling definite with partial eversion of the upper and lower eyelids essentially equivalent. This can be easily ascertained by looking at the animal head-on and noticing the positioning of the eyelids; if the eye margins do not meet, eversion has occurred (Eye lids appear half-closed) |
| +4 | Severe: if eversion of the upper eyelid is pronounced with less pronounced eversion of the lower eyelid, and it is difficult to retract the lids and observe the perilimbal region (eye lids appear more than half-closed), add the comment "Extreme" to the numerical score |

Discharge

| Score | Description |
|---|---|
| 0 | Normal: no discharge |
| +1 | Mild: discharge above normal and present on the inner portion of the eye but not on the lids or hairs of the eyelids. One can ignore the small amount that is in the inner and outer canthus if it has not been removed prior to starting the study |
| +2 | Moderate: discharge is abundant, easily observed, and has collected on the lids and around the hairs of the eyelids |
| +3 | Severe: discharge has been flowing over the eyelids to wet the hairs substantially on the skin around the eye |

NOTE:
Watery fluid from the eye seen immediately after instillation that does not accumulate or substantially wet the hair around the eye is not graded. Tearing (clear watery fluid seen in the cul-de-sac of the lower lid and/or wetting the hair just below the eye) is noted but not graded.

The tables below summarize the incidences of gross ocular observations in the two groups of rabbits. "Pre" refers to the incidence of gross ocular observations prior to initiation of the study.

TABLE 6

Group 1
n = 5

| Day # | Ocular Discomfort +1 (minimal)*, Duration +1 | | Hyperemia +1 (mild)* | | Swelling | | Discharge | |
|---|---|---|---|---|---|---|---|---|
| | OS | OD | OS | OD | OS | OD | OS | OD |
| pre | 0 | 0 | 0 | 1 | 0 | 0 | 0 | 0 |
| 1 | 0 | 0 | 0 | 0 | 0 | 0 | 0 | 0 |
| 2 | 2 | 0 | 1 | 1 | 0 | 0 | 0 | 0 |
| 3 | 1 | 0 | 1 | 0 | 0 | 0 | 0 | 0 |
| 4 | 0 | 0 | 2 | 0 | 0 | 0 | 0 | 0 |
| 5 | 2 | 0 | 0 | 0 | 0 | 0 | 0 | 0 |

*There were no reports of ocular discomfort or hyperemia greater than +1.

TABLE 7

Group 2
n = 5

| Day # | Ocular Discomfort +1 (minimal)*, Duration +1 | | Hyperemia +1 (mild)* | | Swelling | | Discharge | |
|---|---|---|---|---|---|---|---|---|
| | OS | OD | OS | OD | OS | OD | OS | OD |
| pre | 0 | 0 | 0 | 0 | 0 | 0 | 0 | 0 |
| 1 | 0 | 0 | 3 | 0 | 0 | 0 | 0 | 0 |
| 2 | 1 | 0 | 3 | 0 | 0 | 0 | 0 | 0 |
| 3 | 2 | 0 | 5 | 0 | 0 | 0 | 0 | 0 |
| 4 | 1 | 0 | 5 | 0 | 0 | 0 | 0 | 0 |
| 5 | 1 | 0 | 0 | 0 | 0 | 0 | 0 | 0 |

*There were no reports of ocular discomfort or hyperemia greater than +1.

Note: In both Tables 6 and 7, the numbers under columns "OS" and "OD" refer to the numbers of rabbits with the respective gross ocular observations in that particular eye.

As shown above, the tested pilocarpine formulation was well tolerated, with some of the treated rabbits showing only minimal ocular discomfort (+1, described as intermittent blinking), and with a minor duration of one to thirty seconds (+1). Similarly, only very mild and transient hyperemia described as "a flushed, reddish color predominantly confined to the palpebral conjunctiva with some perilimbal injection but primarily confined to the lower and upper parts of the eye from the 4 and 7 o'clock and the 11 and 1 o'clock positions" (+1 on the scale). No rabbits were observed to experience any swelling or discharge, or for that matter elevated ocular discomfort or hyperemia above +1 on the respective scales.

Example 6

Clinical Study C and Analysis

A clinical study was conducted to compare and evaluate ocular blur and discomfort for two concentrations of pilocarpine hydrochloride (Formulations 3 and 4 in Table 4) to a commercially marketed 1% pilocarpine hydrochloride formulation, manufactured by Sandoz. This 1% Sandoz pilocarpine formulation—hereinafter referred to as "commercial pilocarpine" or "1% commercial pilocarpine"—was also tested in Example 4 and contains the same ingredients mentioned previously (including Hypromellose 2910, a viscosity-enhancing polymer). Five patients passed the initial screening visit and continued in the clinical study.

Figure 10:
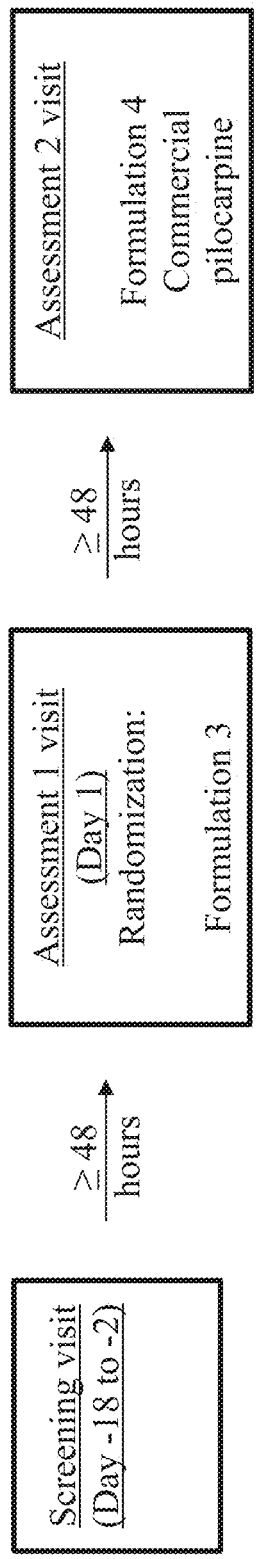
FIG. 10 shows the scheme of the study design in Clinical Study C.

Study procedures: With reference to the study design illustrated in FIG. 10, the study consisted of a Screening visit followed by two Assessment visits. Treatments were administered by a different investigator than those administering questionnaires, so as to mask investigators to results of the study until its completion. Participants were also masked to the study treatments.

At the Screening visit, participants provided informed consent, took a urine pregnancy test (women of childbearing potential only), provided relevant medical/ophthalmic history, had their vision and intraocular pressures measured, and underwent biomicroscopic and dilated retinal exams. Adverse events were queried, and eligible participants were then enrolled in the study.

The Assessment 1 visit occurred after at least 48 hours and up to 18 days following the Screening visit. Participants were randomized to receive Formulation 3 (1% pilocarpine) in the right or left eye, and 1% commercial pilocarpine in the contralateral eye. This assignment was continued on a per-patient basis throughout the study (except that as noted below, Formulation 4 replaced Formulation 3 at Assessment 2). The Assessment 1 visit involved a baseline biomicroscopic examination and a baseline Ocular Discomfort and Blurry Vision Questionnaire assessment (both detailed below). One drop of Formulation 3 was instilled in the randomized eye, and one drop of commercial pilocarpine 1% was instilled in the contralateral eye. The Ocular Discomfort and Blurry Vision Questionnaire was performed prior to drop instillation and at 30 seconds, 1 minute, 90 seconds, 2 minutes, 3 minutes, 4 minutes and 5 minutes after drop instillation, and answered simultaneously for both eyes independently. Biomicroscopic examination was performed at 5 minutes and 60 minutes in both eyes. Adverse Effects (AEs) were also assessed.

The Assessment 2 visit occurred after at least 48 hours and up to 6 months following the Assessment 1 visit. This assessment compared the same in-eye characteristics as those evaluated in Assessment 1 using a slightly higher dose of the pilocarpine hydrochloride (i.e. 1.25%, Formulation 4) versus 1% commercial pilocarpine. The same eye randomly assigned to Formulation 3 at the Assessment 1 visit received Formulation 4 at the Assessment 2 visit. The procedures of Assessment 2 were otherwise the same as in Assessment 1. Participants exited the study at the end of the Assessment 2 visit.

Detailed Diagnostic Ocular Procedures: A biomicroscopy (slit lamp) examination was performed to assess the ocular surface including the cornea, conjunctiva, and eyelids in both eyes and pathology was graded on scale of 0 (none) to 4 (severe).

The intraocular pressure (IOP) measurement was performed at a slit lamp with a Goldmann Tonometer in both eyes. One drop of an anesthetic agent (either Proparacaine 0.5% or Tetracaine 0.5%) was instilled in both eyes, and a fluorescein strip applied to the tear film in inferior fornix. Gentle applanation on the cornea with the tonometer was performed to measure the IOP and the results recorded in mmHg.

The pupils in both eyes were dilated with one drop of tropicamide eye drops and one drop of 2.5% phenylephrine, and repeated as needed 5 to 15 minutes later until the pupils were adequately dilated. A dilated Retinal Examination was performed using an indirect ophthalmoscope with a Volk 28D or Volk 20D lens for examination of the retinal periphery and the slit lamp with the Volk Super Field NC lens or 90D lens for examination of the posterior pole. Any retinal pathology was graded on scale of 0 (none) to 4 (severe).

Detailed Ocular Discomfort and Blurry Vision Questionnaire Procedure: Ocular Discomfort and Blurry Vision Questionnaires were conducted in Assessment 1 and 2 at baseline, then at 30 seconds, 1 minute, 90 seconds, 2 minutes, 3 minutes, 4 minutes and 5 minutes after instillation of the study drug. The questionnaires consist of two visual analog scales ("VAS") to assess the degree of the participant's ocular discomfort and blurry vision. Participants were instructed to mark a vertical line on the anchored VAS that best captures how their eyes were feeling at the current moment. A trained member of the study personnel then used a provided ruler to convert the participant's response to a numerical value (0 to 100). This evaluation was conducted simultaneously for each eye independently. The questionnaire read as follows (Note: The VAS scales were an actual scale and not just text as indicated below):

Think about how each eye is feeling right now. Then, using the scales provided below, please mark a vertical line that best describes your experience with these symptoms:

Blurry vision (VAS anchors: 0=no blurry/vision, 100=maximum blurry vision)

Ocular discomfort (VAS anchors: 0=no ocular discomfort, 100=maximum ocular discomfort)

Ocular hyperemia was also evaluated at baseline, five minutes post-assessment, and 60 minutes post-assessment during both Assessments 1 and 2. Hyperemia was also assessed once during the initial screening process. Such hyperemia was assessed on a five-point scale as a component of the biomicroscopy evaluation, with the scoring being graded as follows: 0=None; +0.5=Trace; +1=Mild; +2=Moderate; +3=Severe. Ocular hyperemia assessments were separately evaluated for the following three areas: eyelid/eyelid margins/eyelash, conjunctiva (bulbar or palpebral), and the cornea.

Results: The results of Clinical Study C showed several unexpected results in favor of the polymer-free Formulations 3 and 4, in contrast with the 1% commercial pilocarpine formulation.

Figure 11A:
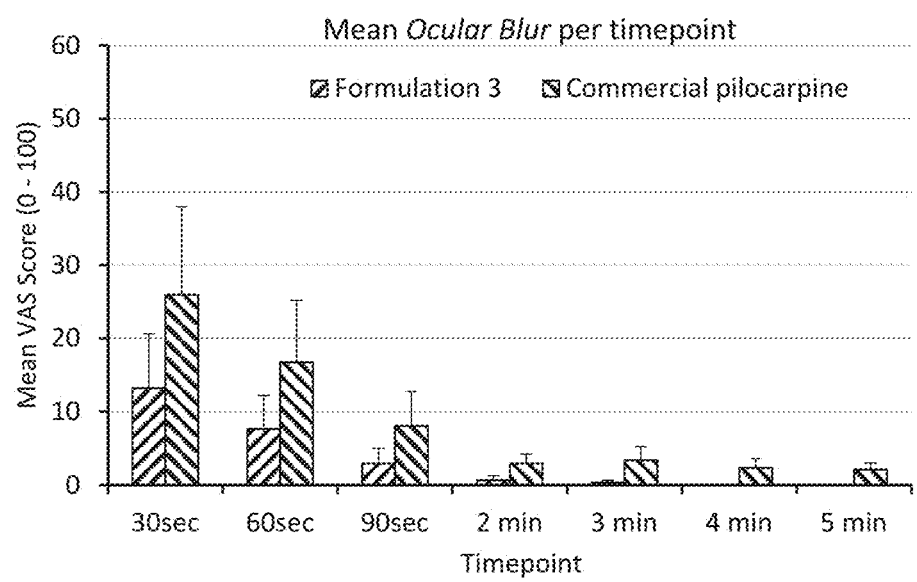
FIGS. 11A and B illustrate the mean ocular blur and ocular discomfort, respectively, per timepoint for the two tested formulations at Assessment 1 in Clinical Study C.
Figure 11B:
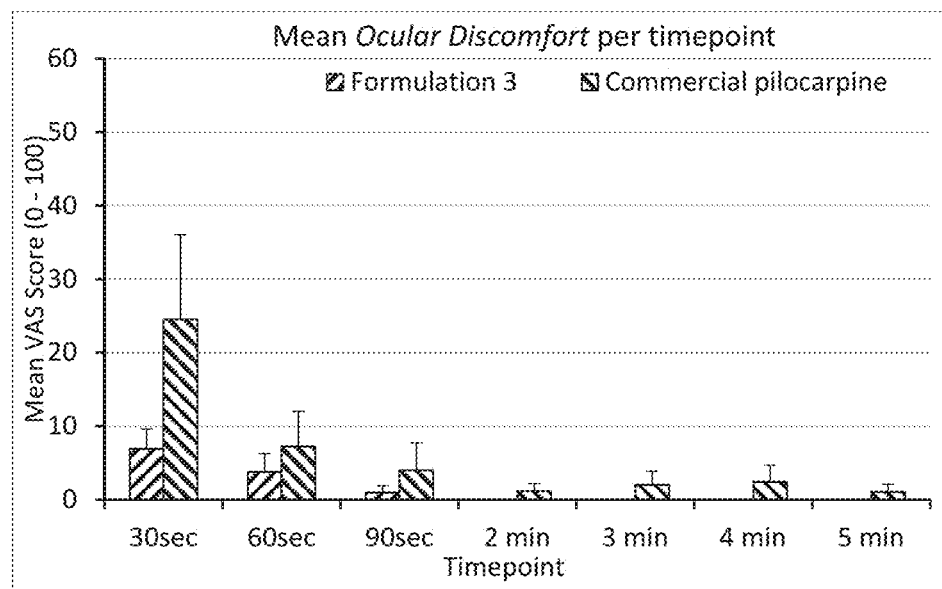
Figure 12A:
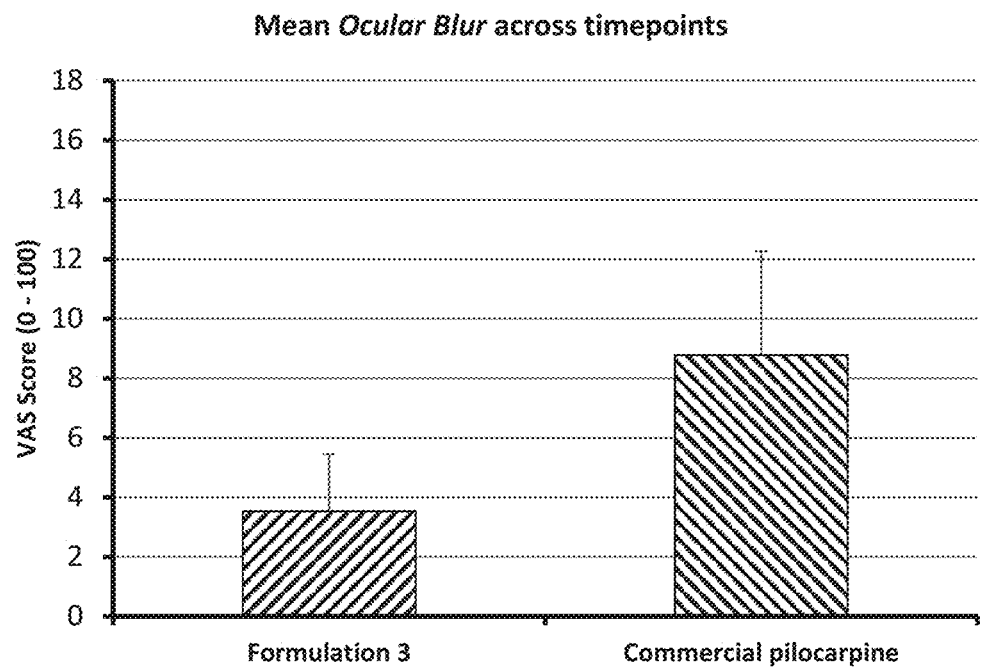
FIGS. 12A and B illustrate the mean ocular blur and ocular discomfort, respectively, across timepoints for the two tested formulations at Assessment 1 in Clinical Study C.
Figure 12B:
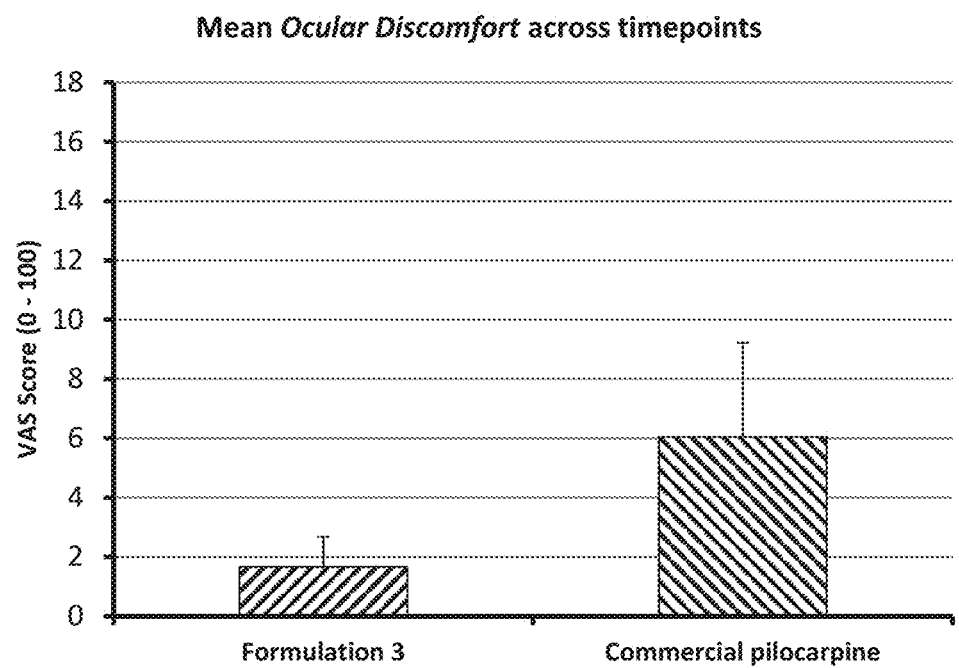

Assessment 1 visit: with reference to FIGS. 11A and 11B, Formulation 3 was shown to demonstrate less ocular blur and ocular discomfort on the VAS scale at each timepoint over five minutes, in comparison with the commercial pilocarpine formulation. Moreover, and with reference to FIG. 12A, Formulation 3 showed significantly less mean ocular blur over a five-minute time period following instillation compared to the commercial pilocarpine formulation (p=0.0156). With reference to FIG. 12B, Formulation 3 showed a numerically lower mean ocular discomfort over a five-minute time period following instillation compared to the commercial pilocarpine formulation (p=0.0966).

Figure 13A:
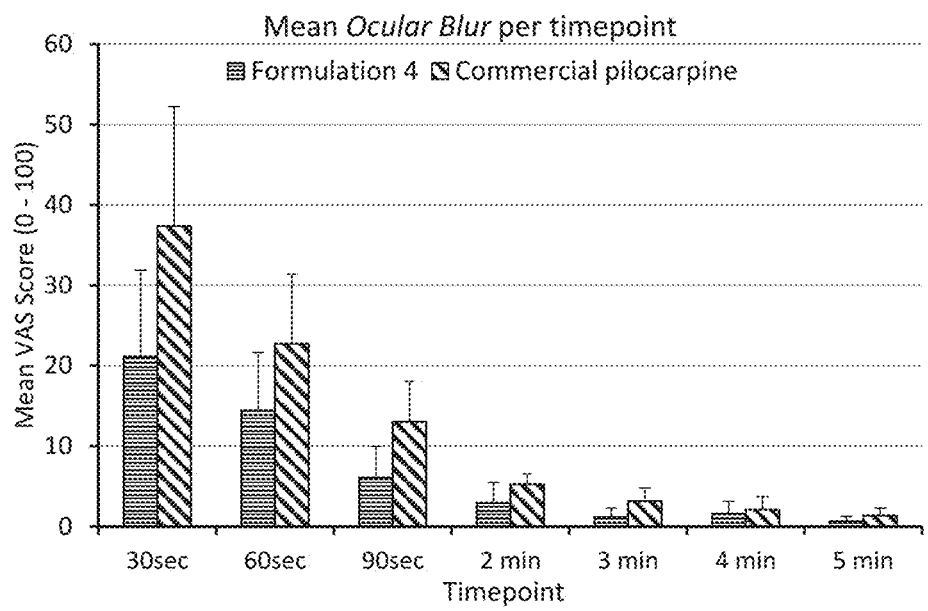
FIGS. 13A and B illustrate the mean ocular blur and ocular discomfort, respectively, per timepoint for the two tested formulations at Assessment 2 in Clinical Study C.
Figure 13B:
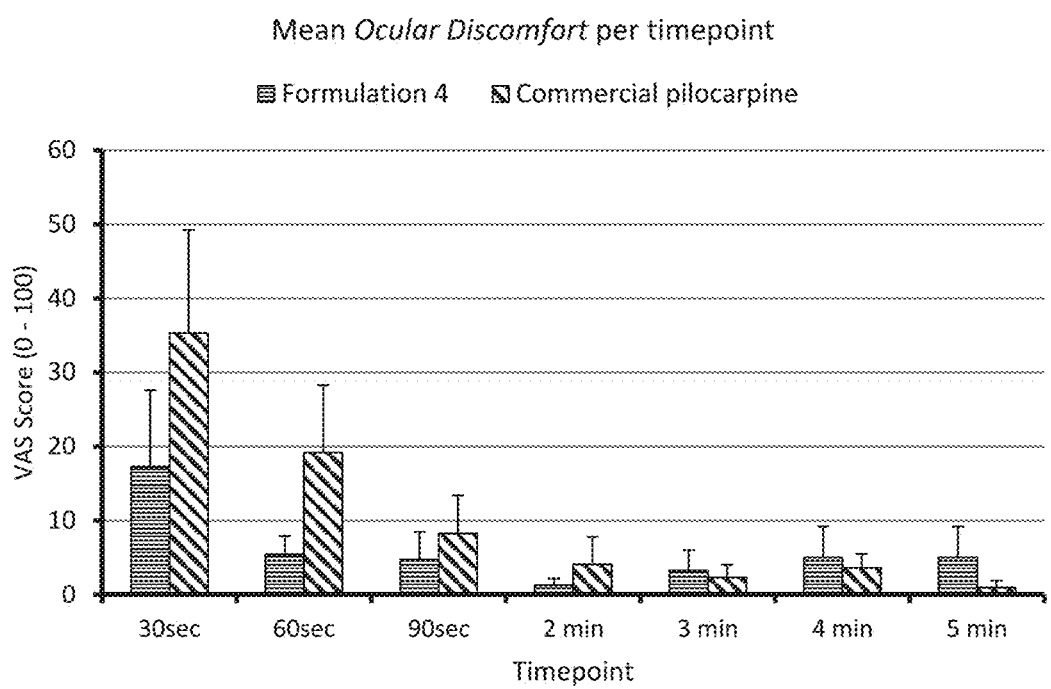
Figure 14A:
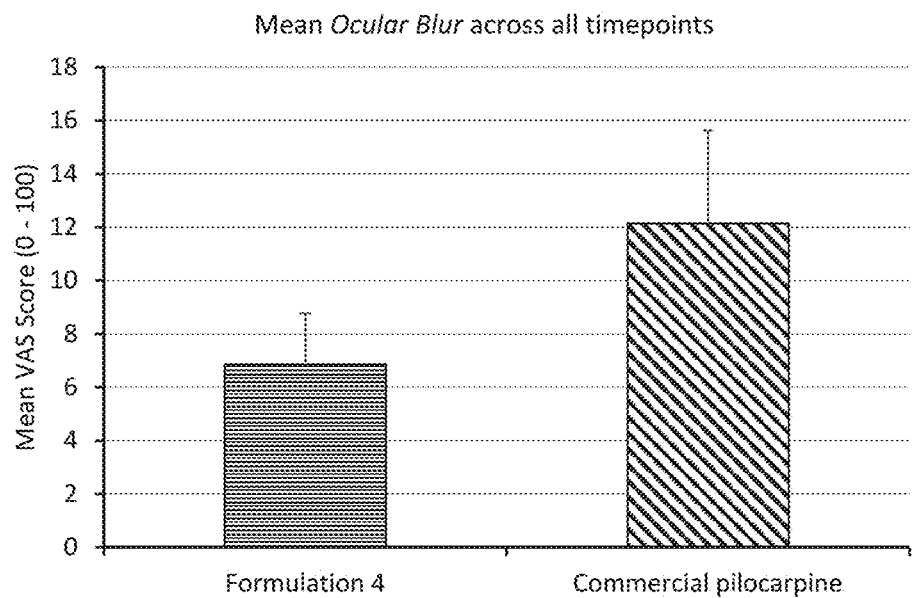
FIGS. 14A and B illustrate the mean ocular blur and ocular discomfort, respectively, across timepoints for the two tested formulations at Assessment 2 in Clinical Study C.
Figure 14B:
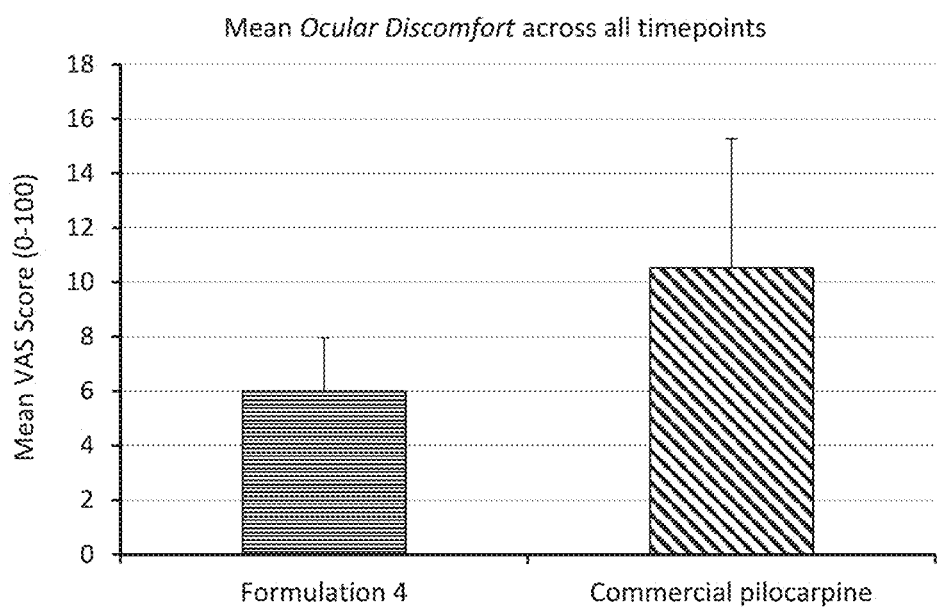

Assessment 2 visit: referring now to FIGS. 13A and B, Formulation 4 was shown to demonstrate less ocular blur on the VAS scale at each timepoint over five minutes, and less initial ocular discomfort for the first four timepoints, in comparison with the commercial pilocarpine formulation. The mean ocular blur over a five-minute time period following instillation was significantly lower for Formulation 4 in comparison to the commercial pilocarpine formulation (p=0.0492), as shown in FIG. 14A. FIG. 14B also shows that Formulation 4 had a numerically lower mean ocular discomfort score across that same time period (p=0.1978).

Safety results: Patient-reported adverse events were tabulated, and are set forth below in Table 8.

TABLE 8

| Adverse Event | 1% Commercial pilocarpine | Formulation 3 | Formulation 4 |
|---|---|---|---|
| Eye pain | 2 | 1 | |
| Brow ache | 3 | | 1 |
| Blurry vision | 5 | | |
| Light sensitivity | 1 | | |
| Stinging | 1 | | |
| Itching | 1 | | |
| Total | 13 | 1 | 1 |

With reference to Table 8, there were surprisingly a much larger number of reported adverse events—13 total—in patient eyes receiving the 1% commercial pilocarpine formulation. By comparison, only one adverse event was reported for each of the patient eyes receiving either Formulation 3 (1% pilocarpine) or Formulation 4 (1.25% pilocarpine). Adverse events such as blurry vision, light sensitivity, stinging, and itching were only seen in the commercial pilocarpine formulation, and such adverse events were not reported for the other two tested formulations. Moreover, the eyes dosed with commercial pilocarpine exhibited higher incidences of hyperemia, for example at five minutes post instillation. At that time period, the mean of non-zero hyperemia scores for the commercial pilocarpine (across both Assessments 1 and 2) was 0.9375. By comparison, the mean of non-zero hyperemia scores for Formulation 3 during Assessment 1 was only 0.75, while Formulation 4 showed a mean non-zero hyperemia score of 0.5 for Assessment 2.

The results of Clinical Study C indicated that polymer-free pilocarpine formulations (Formulations 3 and 4) unexpectedly showed far lower incidences of blurring and ocular discomfort in comparison with the tested 1% commercial pilocarpine formulation which contained polymers. These results were particularly unexpected for Formulation 4, which contained a higher amount of pilocarpine than the commercial pilocarpine formulation. Moreover, the incidence of adverse events and hyperemia was greater in the commercial pilocarpine formulation versus either Formulations 3 and 4. At the same time, although ocular blurring and ocular discomfort were slightly higher for Formulation 4 versus Formulation 3, these were minor increases in comparison to the much greater blurring and discomfort seen with the commercial pilocarpine formulation.

Without wishing to be bound by theory, it is possible that the differences between the commercial pilocarpine and the two other tested formulations are due at least in part to the viscosity-enhancing polymers found in the commercial pilocarpine formulation. Such ingredients, typically used to increase residence time on the ocular surface so as to reduce the need to administer pilocarpine multiple times a day for effective glaucoma treatment, appear to have a hitherto unrecognized effect on reducing the tolerability of pilocarpine. These findings also surprisingly stand at odds with conventional wisdom, where those same polymers (e.g., hypromellose) are often added into ocular formulations so as to increase ocular comfort. The opposite appears to be the case, as seen in the previously-described results where the polymer-free compositions achieved greater ocular comfort.

Here, the amounts of pilocarpine found to be effective for the improvement of vision parameters or treating certain ocular conditions (e.g., presbyopia) mean that effective improvement or treatment is possible without requiring the polymers typically found in pilocarpine preparations for glaucoma. Additionally, even with a 25% higher concentration of pilocarpine used Formulation 4 (1.25%), this formulation nevertheless showed a lower incidence of ocular blurring, ocular discomfort, adverse events, and hyperemia compared to the 1% commercial pilocarpine formulation, while at the same time improving vision parameters and/or treating ocular conditions such as presbyopia better than formulations containing differing amounts of pilocarpine.

Example 7

Clinical Study D

A Phase 3, multicenter, double-masked, randomized, vehicle-controlled, parallel-group study is conducted to evaluate the efficacy, safety, and pharmacokinetics of Formulation 4 (1.25% pilocarpine) dosed once daily and bilaterally, over a period of 30 days in participants with presbyopia.

The study population consists of adult male and female participants with objective and subjective evidence of presbyopia, and approximately 266 participants are enrolled. Participants are randomized in a 1:1 ratio to receive either Formulation 4 or vehicle dosed once daily, in each eye, for 30 days. This randomization is stratified by age (two groups: ≤50 years and >50 years), baseline binocular DCNVA (two groups: 20/40 to 20/60 inclusively, and worse than 20/60), iris color (brown and non-brown), and emmetropes/non-emmetropes. This study consists of the following visits: screening (Days −30 to −1), Day 1 (baseline), and Days 3, 7, 14, and 30.

Efficacy is evaluated using measures of mesopic and photopic high contrast distance-corrected near visual acuity ("DCNVA") and high contrast distance-corrected intermediate visual acuity ("DCIVA") for each eye and binocularly. Additionally, mesopic and photopic pupil diameter (distance and near) are evaluated, as well as depth of focus and patient-reported outcome questionnaires. These questionnaires include the following: Mesopic and Photopic Near Vision Presbyopia Task-based Questionnaire, Presbyopia Impact and Coping Questionnaire, Presbyopia Patient Satisfaction Questionnaire, Single-Item Patient Global Impression of Change, Single-Item Patient Global Impression of Status, and Single-Item Patient Expectations for Treatment Efficacy.

Safety and tolerability are evaluated by eliciting adverse events, as well as photopic and mesopic high contrast corrected distance visual acuity for each eye and binocularly, near contrast sensitivity, vital signs (blood pressure and heart rate), study drug tolerability and drop comfort assessments, temporal/supraorbital headache (visual analog scale), intraocular pressure, slit-lamp biomicroscopy, manifest refraction, dilated funduscopic examination, and a pregnancy test for women of childbearing potential (during screening). Pharmacokinetics are also evaluated by testing plasma concentrations of pilocarpine at selected sites.

The results of this study show that 1.25% pilocarpine hydrochloride administered once daily is safe and effective for the improvement of at least one vision parameter (e.g., near vision acuity, distance vision acuity, etc.) and/or at least one ocular condition (e.g., presbyopia).

Non-limiting examples in accordance with the present invention are as follows.

Example 8

A 42-year old woman complains of an increasing inability to focus on text when reading documents at work. The woman is seen by an ophthalmologist who performs a visual acuity test in which she is asked to read lines of letters on an eye chart without the assistance of glasses or contacts (neither of which she wears). She finds that she is only able to read the first four lines on the chart, when a person with normal vison should be able to read six. Based on the woman's age and results of the test, she is diagnosed with presbyopia. The woman is reluctant to have to obtain reading glasses or wear contact lenses and asks if there are any other medical treatments. She is instructed to administer to her eyes the composition of Formulation 4, as set out in Table 4, once daily. After administration of the dose, she finds that her vision improves. On a follow-up visit to the ophthalmologist and after having again administered Formulation 4 to her eyes, she is again asked to read lines of letters on an eye chart. This time, she is able to read the first six lines on the chart, a two-line improvement over her previous results. She experienced no eye discomfort or hyperemia from the eye drop.

Example 9

A 66-year old man reports dissatisfaction with his bifocal glasses, which, due to the two different refractive indices in the component parts of the lenses, have caused him to nearly fall several times when descending stairs. His ophthalmologist, having previously diagnosed him with presbyopia, instructs him to administer once daily to his eyes a pilocarpine hydrochloride formulation as set forth in Table 4. After administration, the patient finds that his near and distance vision are improved, and that he no longer requires near and distance visual correction with glasses.

Example 10

A 31-year old man has been diagnosed with hyperopia, and consequently has difficulty reading documents and other text at a close distance (e.g., at arm's length from the body), especially in dim lighting. After a visit to his optometrist, who prescribes him a polymer-free 1.25% w/v pilocarpine hydrochloride ophthalmic formulation for once daily use, he finds that his near vision is improved. Moreover, he finds that he is able to see more easily in dim lighting and while driving at night.

Example 11

As a result of a car accident, a 40-year old woman experienced head trauma that resulted in some nerve injury manifesting partly as anisocoria, with the pupil in her left eye being larger than the right. The resulting photosensitivity due to her increased pupil size causes discomfort. Her doctor instructs her to instill a pilocarpine hydrochloride formulation into the affected eye. The miotic effect reduces her ocular discomfort and treats the anisocoria.

Example 12

A 36-year old woman complains of difficulties reading text at near and far distances. After a visual acuity test, her optometrist diagnoses her as having decreased visual acuity due to a combination of myopia and astigmatism. Because she does not want to wear glasses, she is prescribed the Formulation 3 (set forth in Table 4). After administration of one drop of the formulation once daily, she returns to the optometrist for a follow-up visit after a week. Here, both her near and distance vision acuity were found to have increased by at least two lines from her baseline visit prior to treatment.

While certain embodiments of the invention have been described, other embodiments may exist. While the specification includes a detailed description, the invention's scope is indicated by the following claims. Furthermore, while the specification has been described in language specific to structural features and/or methodological acts, the claims are not limited to the features or acts described above. Rather, the specific features and acts described above are disclosed as illustrative aspects and embodiments of the invention. Various other aspects, embodiments, modifications, and equivalents thereof which, after reading the description herein, may suggest themselves to one of ordinary skill in the art without departing from the spirit of the present invention or the scope of the claimed subject matter.

What is claimed is:

1. A method for the treatment of presbyopia in a patient in need thereof, comprising
    topically administering once daily to at least one eye of the patient one drop of a pharmaceutically acceptable ophthalmic composition comprising 1.25% w/v pilocarpine hydrochloride as the sole active ingredient, 1.0% w/v boric acid, 0.015% w/v sodium citrate dihydrate, 0.08% w/v sodium chloride, 0.0075% w/v benzalkonium chloride, and water, and wherein the pH of the ophthalmic composition is between 3.0 to 5.5, and wherein the viscosity of the ophthalmic composition is 1 centipoise; and
  wherein the administration of the pharmaceutically acceptable ophthalmic composition to the patient results in a greater improvement in near visual acuity without reduction of distance visual acuity as compared to administration of one drop of a second pharmaceutically acceptable ophthalmic composition comprising the same ingredients as the first pharmaceutically acceptable ophthalmic composition but with 0.5% w/v or less pilocarpine hydrochloride.

2. The method of claim 1, wherein the method results in an improvement from baseline under the condition of mesopic, high contrast near vision acuity.

3. The method of claim 1, wherein the method results in an improvement from baseline under the condition of photopic, high contrast near vision acuity.

4. The method of claim 1, wherein the method results in an improvement from baseline under the condition of mesopic, high contrast distance vision acuity.

5. The method of claim 1, wherein the method results in an improvement from baseline under the condition of photopic, high contrast intermediate vision acuity.

6. The method of claim 1, wherein the method results in an improvement from baseline under the condition of mesopic, high contrast intermediate vision acuity.

7. The method of claim 1, wherein the method results in an improvement from baseline under the condition of photopic, high contrast intermediate vision acuity.

8. The method of any one of claims 2 to 7, wherein the improvement from baseline has a duration of effect of at least two hours.

9. The method of any one of claims 2 to 7, wherein the improvement from baseline has a duration of effect of at least six hours.

10. A method for the treatment of presbyopia in a patient in need thereof, comprising
    topically administering once daily to at least one eye of the patient one drop of a pharmaceutically acceptable ophthalmic composition consisting of 1.25% w/v pilocarpine hydrochloride as the sole active ingredient, 1.0% w/v boric acid, 0.015% w/v sodium citrate dihydrate, 0.08% w/v sodium chloride, 0.0075% w/v benzalkonium chloride, and water, and wherein the pH of the ophthalmic composition is between 3.0 to 5.5, and wherein the viscosity of the ophthalmic composition is 1 centipoise; and wherein the administration of the pharmaceutically acceptable ophthalmic composition to the patient results in a greater improvement in near visual acuity without reduction of distance visual acuity as compared to administration of one drop of a second pharmaceutically acceptable ophthalmic composition comprising the same ingredients as the first pharmaceutically acceptable ophthalmic composition but with 0.5% w/v or less pilocarpine hydrochloride.

11. The method of claim 10, wherein the method results in an improvement from baseline under the condition of mesopic, high contrast near vision acuity.

12. The method of claim 10, wherein the method results in an improvement from baseline under the condition of photopic, high contrast near vision acuity.

13. The method of claim 10, wherein the method results in an improvement from baseline under the condition of mesopic, high contrast distance vision acuity.

14. The method of claim 10, wherein the method results in an improvement from baseline under the condition of photopic, high contrast intermediate vision acuity.

15. The method of claim 10, wherein the method results in an improvement from baseline under the condition of mesopic, high contrast intermediate vision acuity.

16. The method of claim 10, wherein the method results in an improvement from baseline under the condition of photopic, high contrast intermediate vision acuity.

17. The method of any one of claims 11 to 16, wherein the improvement from baseline has a duration of effect of at least two hours.

18. The method of any one of claims 11 to 16, wherein the improvement from baseline has a duration of effect of at least six hours.

19. A method for the treatment of presbyopia in a patient in need thereof, comprising topically administering twice daily to at least one eye of the patient one drop of a pharmaceutically acceptable ophthalmic composition comprising 1.25% w/v pilocarpine hydrochloride as the sole active ingredient, 1.0% w/v boric acid, 0.015% w/v sodium citrate dihydrate, 0.08% w/v sodium chloride, 0.0075% w/v benzalkonium chloride, and water, and wherein the pH of the ophthalmic composition is between 3.0 to 5.5, and wherein the viscosity of the ophthalmic composition is 1 centipoise; and wherein the administration of the pharmaceutically acceptable ophthalmic composition to the patient results in a greater improvement in near visual acuity without reduction of distance visual acuity as compared to administration of one drop of a second pharmaceutically acceptable ophthalmic composition comprising the same ingredients as the first pharmaceutically acceptable ophthalmic composition but with 0.5% w/v or less pilocarpine hydrochloride.

20. The method of claim 19, wherein the method results in an improvement from baseline under the condition of mesopic, high contrast near vision acuity.

21. The method of claim 19, wherein the method results in an improvement from baseline under the condition of photopic, high contrast near vision acuity.

22. The method of claim 19, wherein the method results in an improvement from baseline under the condition of mesopic, high contrast distance vision acuity.

23. The method of claim 19, wherein the method results in an improvement from baseline under the condition of photopic, high contrast intermediate vision acuity.

24. The method of claim 19, wherein the method results in an improvement from baseline under the condition of mesopic, high contrast intermediate vision acuity.

25. The method of claim 19, wherein the method results in an improvement from baseline under the condition of photopic, high contrast intermediate vision acuity.

26. The method of any one of claims 20 to 25, wherein the improvement from baseline has a duration of effect of at least two hours.

27. The method of any one of claims 20 to 25, wherein the improvement from baseline has a duration of effect of at least six hours.

28. A method for the treatment of presbyopia in a patient in need thereof, comprising topically administering twice daily to at least one eye of the patient one drop of a pharmaceutically acceptable ophthalmic composition consisting of 1.25% w/v pilocarpine hydrochloride as the sole active ingredient, 1.0% w/v boric acid, 0.015% w/v sodium citrate dihydrate, 0.08% w/v sodium chloride, 0.0075% w/v benzalkonium chloride, and water, and wherein the pH of the ophthalmic composition is between 3.0 to 5.5, and wherein the viscosity of the ophthalmic composition is 1 centipoise; and wherein the administration of the pharmaceutically acceptable ophthalmic composition to the patient results in a greater improvement in near visual acuity without reduction of distance visual acuity as compared to administration of one drop of a second pharmaceutically acceptable ophthalmic composition comprising the same ingredients as the first pharmaceutically acceptable ophthalmic composition but with 0.5% w/v or less pilocarpine hydrochloride.

29. The method of claim 28, wherein the method results in an improvement from baseline under the condition of mesopic, high contrast near vision acuity.

30. The method of claim 28, wherein the method results in an improvement from baseline under the condition of photopic, high contrast near vision acuity.

31. The method of claim 28, wherein the method results in an improvement from baseline under the condition of mesopic, high contrast distance vision acuity.

32. The method of claim 28, wherein the method results in an improvement from baseline under the condition of photopic, high contrast intermediate vision acuity.

33. The method of claim 28, wherein the method results in an improvement from baseline under the condition of mesopic, high contrast intermediate vision acuity.

34. The method of claim 28, wherein the method results in an improvement from baseline under the condition of photopic, high contrast intermediate vision acuity.

35. The method of any one of claims 29 to 34, wherein the improvement from baseline has a duration of effect of at least two hours.

36. The method of any one of claims 29 to 34, wherein the improvement from baseline has a duration of effect of at least six hours.

* * * * *